(12) United States Patent
Nudler et al.

(10) Patent No.: US 7,767,232 B2
(45) Date of Patent: Aug. 3, 2010

(54) CONTROL OF NITRIC OXIDE BIOACTIVITY BY PERFLUOROCARBONS

(75) Inventors: Evgeny Nudler, New York, NY (US); Ruslan Rafikova, Brooklyn, NY (US); Olga Rafikova, Brooklyn, NY (US)

(73) Assignee: New York University, New York, NY (US)

( * ) Notice: Subject to any disclaimer, the term of this patent is extended or adjusted under 35 U.S.C. 154(b) by 1025 days.

(21) Appl. No.: 10/663,693

(22) Filed: Sep. 17, 2003

(65) Prior Publication Data
US 2004/0127425 A1    Jul. 1, 2004

Related U.S. Application Data

(60) Provisional application No. 60/411,828, filed on Sep. 19, 2002.

(51) Int. Cl.
*A61K 33/14* (2006.01)
*A61K 33/16* (2006.01)
*A61K 31/02* (2006.01)
*A61K 31/035* (2006.01)

(52) U.S. Cl. ............... 424/673; 424/718; 514/743; 514/746; 514/759

(58) Field of Classification Search ............ 514/746, 514/743, 759; 424/673, 718
See application file for complete search history.

(56) References Cited

U.S. PATENT DOCUMENTS

| | | | |
|---|---|---|---|
| 5,514,720 A | 5/1996 | Clark, Jr. et al. | |
| 5,621,144 A | 4/1997 | Cooper | |
| 5,684,050 A | 11/1997 | Clark, Jr. et al. | |
| 5,869,539 A | 2/1999 | Garfield et al. | |
| 6,166,092 A | 12/2000 | Sekins et al. | |
| 6,204,296 B1 | 3/2001 | Weers et al. | |
| 6,289,892 B1 | 9/2001 | Faithfull et al. | |

OTHER PUBLICATIONS

Olga Rafikova et al., Control of Plasma Nitric Oxide Bioactivity by Perfluorocarbons; Circulation 2004; 110; pp. 3573-3580; Amercan Heart Association.*
"Regulation of Basal Myocardial Function by NO," *Cardiovascular Research*, Georg Kojda et al, 1999.
"Potential Therapeutic Uses for S-Nitrosothiols," *Clinical Science*, G. Richardson et al, 2002.
"S-Nitrosothiols: A Class of Nitric Oxide-Donor Drugs," *Clinical Science*, Haitham Al-Sa'Doni et al, 2000.
"Selective Pharmacological Inhibition of Distinct Nitric Oxide Synthase Isoforms," *Biochemical Pharmacology*, vol. 51, Garry J. Southan et al, 1996.
"Effects of Nitric Oxide Synthase Blockers on Renal Function," *Nephrol Dial Transplant*, Francis B. Gabbai, 2001.
"Is Nitric Oxide Overproduction the Target of Choice for the Management of Septic Shock?," *Pharmacology & Therapeutics*, vol. 91, Francois Feihl et al, 2001.
Ignarro, L. J. et al., "Mechanism of vascular smooth muscle relaxation by organic nitrates, nitrites, nitro-prusside, and nitric oxide: evidence for the involvement of S-nitrosthiols as active intermediates", J. Pharmacol. Exp. Ther., vol. 218, No. 3, pp. 739-749 (1981).
Keaney, J.F. Jr, et al., "NO forms an adduct with serum albumin that has endothelium-derived relaxing factor-like properties", J. Clin. Invest. vol. 91, pp. 1582-1589 (1993).
Clancy, R.M.,et al., "Nitric oxide reacts with intracellular glutathione and activates the hexose monophosphate shunt in human neutrophils: evidence for S-nitrosoglutathione as a bioactive intermediary", Proc. Natl. Acad. Sci. U.S.A., vol. 91, pp. 3680-3684 (1994).
Gaston, B., et al., "Bronchodilator S-nitrosothiol deficiency in asthmatic respiratory failure", Lancet, vol. 351, pp. 1317-1319, (1998).
Hogg, N., "Biological chemistry and clinical potential of S-nitrosothiols", Free. Radic. Biol. Med., vol. 28, No. 10, pp. 1478-1486 (2000).
Al-Sa'Doni, H. et al., "S-Nitrosothiols: a class of nitric oxide-donor drugs", Clin. Sci. (Lond), vol. 98, pp. 507-520 (2000).
Napoli, et al., "Efficacy and age-related effects of nitric oxide-releasing aspirin on experimental restenosis", Proc Natl Acad Sci U S A., vol. 99, 1689-1694 (2002).
Spahn, D. R., "Blood Substitutes. Artificial oxygen carriers: perfluorocarbon emulsions", Crit. Care, vol. 3, pp. R93-97 (1999).
Blantz, R.C., et al., "Role of nitric oxide in inflammatory conditions", Nephron, vol. 90, pp. 373-378 (2002).
Chabielska, E. et al., "Losartan inhibits experimental venous thrombosis in spontaneously hypertensive rats", Thromb Res., vol. 90, pp. 271-278 (1998).

(Continued)

*Primary Examiner*—James O Wilson
*Assistant Examiner*—Ebenezer Sackey
(74) *Attorney, Agent, or Firm*—Browdy and Neimark, PLLC

(57) ABSTRACT

Perfluorocarbons are used to control nitric oxide metabolism, either to inhibit nitric oxide activity or to potentiate the effects of nitric oxide. Perfluorocarbons can be used, for example, to treat hypotension and vasoplegia in septic shock, to protect against myocardial ischemia-reperfusion injury, to treat hypertension, and to provide antiplatelet effects.

16 Claims, 9 Drawing Sheets

OTHER PUBLICATIONS

Sasaki, N. et al., "Activation of mitochondrial ATP-dependent potassium channels by nitric oxide", Circulation, vol. 101, pp. 439-445 (2000).

Richardson, et al., "Potential therapeutic uses for S-nitrosothiols". Clin. Sci. (Lond)., vol. 102, pp. 99-105 (2002).

Gabbai, "Effects of nitric oxide synthase blockers on renal function", Nephrol. Dial. Transplant., vol. 16 (Suppl 1), pp. 10-13 (2001).

Hemmer, K., et al., "An in vitro model for the study of Microglia-Induced Neurodegeneration: involvement of nitric oxide and tumor necrosis factor-alpha", Neurochem. Int., vol. 38(7), pp. 557-565 (2001). Abstract Only.

Law, A. et al., "Say NO to Alzheimer's Disease: the putative links between nitric oxide and dementia of the Alzheimer's type", Brain Res. Brain Res. Rev., vol. 35, No. 1, pp. 73-96 (2001). Abstract Only.

De La Torre, J.C. et al., "Evidence that Alzheimer's disease is a microvascular disorder: the role of constitutive nitric oxide", Brain Res. Brain Res. Rev., vol. 34, No. 3, pp. 119-136 (2000). Abstract Only.

Hartlage-Rubsamen, M. et al., "Fibrillary beta-amyloid deposits are closely associated with atrophic nitric oxide synthase (NOS)-expressing neurons but do not upregulate the inducible NOS in transgenic Tg2576 mouse brain with Alzheimer pathology", Neurosci. Lett., vol. 302, Nos. 2-3, pp. 73-76, (2001). Abstract Only.

Dawson, V. L., et al., "Nitric Oxide Neurotoxicity", J. Chem. Neuroanat., vol. 10, Nos. 3-4, pp. 179-190 (1996). Abstract Only.

Simonian, N. A., et al., "Oxidative stress in neurodegenerative diseases". Annu. Rev. Pharmacol. Toxicol., vol. 36, pp. 83-106 (1996). Abstract Only.

* cited by examiner

Thiols

1) R-SH         ( R- aromatic, alkyl, peptidil etc)
cystein, homocystein, glutathione 2)  1,2-dithiols 3)  1,3-dithiols  (α-lipoic acid)

4) Three thiols?

5)

Tryptophane like serotonin melatonin

Piridine, heterocyclic like

Antioxidants

α - tocopherrol

CONTROL OF NITRIC OXIDE BIOACTIVITY BY PERFLUOROCARBONS

CROSS-REFERENCE TO RELATED APPLICATIONS

The present application claims priority from provisional application Ser. No. 60/411,828, filed Sep. 9, 2002. The entire contents of which are hereby incorporated by reference.

FIELD OF THE INVENTION

The present invention is directed to the use of perfluorocarbons to regulate bioactivity of nitric oxide in animals, either to inhibit the activity of nitric oxide or to enhance the activity of nitric oxide.

BACKGROUND OF THE INVENTION

Nitric oxide is synthesized enzymatically from L-arginine by almost all tissues of the body, including brain, peripheral nervous system, smooth muscle, kidney, vascular, lung, uterus, etc. Nitric oxide is involved in many vascular functions including vasorelaxation and blood clotting. (Moncada et al., 1993). Heme proteins such as guanylyl cyclase serve as primary targets for nitric oxide (Bredt et al., 1994).

There is a substantial body of evidence from animal and human studies that a deficiency in nitric oxide contributes to the pathogenesis of a number of diseases, including hypertension, artherosclerosis, and diabetes.

Depending upon the rate, timing, and spatial distribution of nitric oxide production, as well as the chemical microenvironment (e.g., presence of ROS, redox status of the cell), nitric oxide acts either as a direct signaling messenger or as an indirect toxic effector via the formation of various reactive nitrogen species. Indeed, both functions may be occurring at the same time, i.e., spatially targeted production of nitric oxide may simultaneously enhance the antimicrobial function of the neutrophil respiratory burst while protecting host cells from oxidant injury and, perhaps, preventing the uncontrolled explosion of the inflammatory response (e.g., down-regulation of nuclear factor κ-B activation). At other times, the cytotoxic potential of reactive nitrogen species may turn against the host, as has been documented in some murine models of infection, such as Influenza A pneumonitis or intestinal and liver injury caused by $T.$ $gondii.$ (Feihl et al., 2001).

Nitric oxide was originally described as the principal endothelium-derived relaxing factor, but it is now known to subserve a variety of functions throughout the body, both physiological and pathophysiological. Among its diverse functions, nitric oxide has been implicated in neurotransmission, immune regulation, vascular smooth muscle relaxation, and inhibition of platelet aggregation.

Nitric oxide has been found to activate soluble guanylate cyclase. Guanylate cyclase exists in two forms in the cell: a soluble isoform within the cytosol and a particulate isoform which is membrane-associated. Purified soluble guanylate cyclase can be activated in vitro by nitric oxide-donating compounds. Once the enzyme has been activated, there is accumulation of cGMP which, in vascular smooth muscle cells, is accompanied by relaxation and hence vasodilation.

In other cell types, the accumulation of cGMP is accompanied by different physiological effects. cGMP can be formed by soluble guanylate cyclase in platelets, following stimulation by nitric oxide derived either from the vascular endothelium or from endothelial-type NOS within the platelets themselves, leading to inhibition of platelet aggregation.

In the central nervous system, nitric oxide can be formed in the postsynaptic nerve cell following activation of N-methyl-D-aspartate (NMDA) receptors by glutamate. This nitric oxide diffuses out and acts upon guanylate cyclase in one or more neighboring neurons, including the presynaptic nerve cells, thus acting as part of a feedback loop. In one model of brain activity, such a retrograde messenger is involved in the building up of long-term memory. In addition, nitric oxide in the brain can act upon nerve cells other than the presynaptic nerve cell, causing a variety of effects: neuroprotection, long-term potentiation (an activity-dependent increase in synaptic strength), and long-term depression (a long-lasting depression of parallel fiber synapses following repeated excitation by climbing fibers of Purkinjie cells). It has also been suggested that overproduction of nitric oxide may cause neurotoxicity and certain degenerative conditions, such as Alzheimer-type dementia, either because of its radical nature or because it can generate peroxynitrite.

Nitric oxide is generated in the course of inflammatory and immune reaction, both by macrophages and by neutrophils. The role of these cells is quite extensive, and includes phagocytic and non-phagocytic destruction of foreign or damaged cells. These processes involve the production of large quantities of nitric oxide, which is cytotoxic.

It is possible that either an overabundance or a deficiency of nitric oxide is involved in many other pathological problems in females, such as preeclampsia, preterm labor, climacterium, pregnancy-induced diabetes, and postpartum hemorrhage. Nitric oxide overabundance or deficiency may also be associated with coronary artery disease, cancer, and behavioral and digestive problems.

Premenopausal women have a lower incidence of cardiovascular disease than men. After menopause, the incidence of cardiovascular disease increases progressively, as the risk of coronary heart disease rapidly increases after cessation of ovarian function. These changes are thought to be hormonally mediated and related to the decrease in production of both estrogen and progesterone. Since nitric oxide is very important in control of vascular function, a decrease in nitric oxide production or action is related to pathophysiological changes in blood vessels, i.e., cardiovascular diseases associated with hypertension and artherosclerosis. The steroid hormones regulate nitric oxide synthesis. Thus, it is believed that nitric oxide may mediate all, or at least some, of the actions of the steroid hormones to prevent cardiovascular disease in premenopausal women. It may thus be possible to administer a nitric oxide donor to prevent cardiovascular disease as part of or instead of hormone replacement therapy, thus minimizing or eliminating any undesirable side effects of hormone replacement therapy.

Nitric oxide is also very much involved in the control of blood clotting. Nitric oxide and its donors are potent inhibitors of coagulation (e.g., reviewed in Richardson G. and Benjamin N. (2002)).

In addition, nitric oxide has been implicated in bone remodeling. Bone remodeling disorders such as osteoporosis and osteoarthritis are frequently associated with perturbations in the interaction between local and systemic bone-remodeling regulatory pathways. Postmenopausal bone loss associated with diminished steroid hormones is correlated with increased levels of cytokines. In addition, both estrogen and progestins are effective in preventing postmenopausal bone loss (Garfield, et al., 1999).

Bone-degrading osteoclasts arise from cells within the monocyte macrophage lineage. Excessive osteoclast activity leads to high levels of bone destructions and osteoporosis.

Although these cells have the unique ability to resorb bone, they share various characteristics with macrophages (Garfield, et al., 1999).

Macrophages release nitric oxide in response to inflammatory cytokines and agents. It has been suggested that osteoclasts, like macrophages, synthesize nitric oxide. In models of osteoporosis, nitric oxide inhibition potentiated the loss of bone mineral density by suppressing osteoclast activity and bone resorption. There have also been studies which demonstrated that nitric oxide is produced by chondrocytes. (Garfield, et al., 1999).

Since inhibition of osteoclastic activity is a major aim in treating and preventing osteoporosis, Paget bone disease and rheumatoid arthritis, nitric oxide donors may be useful in treating and preventing these conditions.

Presently, there are only three nitric oxide donor compounds that are used clinically: nitroglycerin, amyl nitrite, and sodium nitroprusside. Nitroglycerin is available in tablets or sprays for sublingual use, intravenously, or in patch form. Amyl nitrite is formulated as an inhalant and is usually used in breakable capsules. Sodium nitroprusside is limited to intravenous infusion. Nitric oxide donors are currently used for treating angina pectoris due to coronary artery disease (nitroglycerin or amyl nitrite) and control of blood pressure associated with myocardial infarction or surgical procedures (nitroglycerin or sodium nitroprusside).

Unfortunately, conventionally available nitric oxide donor compounds have a short duration of action, a short half-life, a lack of tissue specificity, development of tolerance, and accumulation of toxic substances (cyanide for sodium nitroprusside).

Nitric oxide is a gas with low solubility in water and aqueous solutions. Although nitric oxide is a free radical that is highly unstable in vivo, it does not interact directly with most biological substrates and commonly used organic solvents.

An important physiologically significant component of nitric oxide biochemistry involves formation of thionitrite esters with free thiols (S-nitrosothiols: RS-No). Low molecular weight S-nitrosothiols, e.g., S-nitrosoglutathione (GS-NO), S-NO-cysteine (S-NO-Cys) and nitroso derivatives of proteins such as albumin and hemoglobin (Hb) exert nitric oxide-like activity in vivo. They cause arterial and venous smooth muscle relaxation, inhibit platelet aggregation, and activate guanylate cyclase (Stamler et al., 1992; Ignarro et al., 1981; Keaney et al., 1993; Stamler, 1992; Scharfstein et al., 1994; Jia et al., 1996).

Vasoactive S-nitrosothiols are known to be generated in vivo (Stamler et al., 1992; Ignarro et al., 1981; Keaney et al., 1993; Stamler, 1992; Scharfstein et al., 1994; Jia et al., 1996; Clancy et al., 1994; Gaston et al., 1998). The originally reported amount of total S-nitrosothiols in human plasma was 7 µM (Stamler et al., 1992). Many subsequent measurements (Rafikova et al., 2002) detected from 40 nM to 1 µM of plasma S-nitrosothiols in humans and rodents under noninflammatory conditions (Hogg et al., 2002; Marzinzig, 1997; Tsikas et al., 1999). Since S-nitrosothiol compounds are relatively stable and can release nitric oxide when required via reactions with transition metal ions or other reducing agents (Singh et al., 1996; Kashiba-Iwatsuki et al., 1997; Aleryani et al., 1998; Nikitovic et al., 1996), they are envisioned as a buffering system that controls intra- and extra-cellular activities of NO and magnify the range of its action. Once formed, S-nitrosothiols can directly transfer the nitrosyl cation ($NO^+$) to another thiol via the so-called transnitrosation reaction, which ensures the dynamic state of S-nitrosothiols in vivo (Ignarro et al., 1981; Jourd'heuil et al., 2000; Tsikas et al., 2001).

The properties of S-nitrosothiols (RSNOs) are similar to those of nitric oxide. They are involved in smooth muscle cell relaxation, platelet deactivation, immunosuppression, neurotransmission, and host defense. Although they have not yet been used therapeutically, there are data to suggest that S-nitrosothiols have a possible place in the management of a variety of diseases.

At present, the only commercially available S-nitrosothiols are S-nitroso-N-acetylpenicillamine (SNAP), N-acetyl-S-nitrosopenicillaminyl-S-nitrosopenicillamine, and GSNA. None of these compounds has as yet been used therapeutically in animals or humans. One of the main problems with using S-nitrosothiols is their unpredictable rate of decomposition in physiological vehicles, which can occur in the presence of copper and other divalent metals, by enzymatic degradation and as a result of transnitrosation.

Other S-nitrosothiols proposed as drugs are SNO-albumin, which acts as a reservoir of nitric oxide. It is formed when transnitrosation occurs between albumin and low-molecular-mass RSNOs, such as GSNO or SNO-cysteine. However, the cysteine residues in native albumin are few and are hidden inside the molecule. Different forms of poly-SNO-albumin have been prepared by covalent modification of albumin prior to nitrosylation.

Poly-SNO-albumin has been shown to inhibit human vascular smooth muscle cell proliferation in culture to a greater extent than both SNO-albumin and the NONOates.

Captopril, an agiotensin-converting enzyme (ACE) inhibitor, is a reduced thiol and can be nitrosated. It still acts as an ACE inhibitor in this form, but it also functions as a nitric oxide donor, being more effective than captopril itself in decreasing acute and chronic elevation of blood pressure in rats. SNO-captopril can also take part in transnitrosation reactions, transferring its nitroso moiety to haem proteins.

Tissue plasminiogen activator (tPA) is another drug used in routine clinical practice that can undergo nitrosation. This has no effect on its catalytic ability, fibrin stimulation, binding to fibrinogen, or interaction with plasminogen activator inhibitor-1. It does, however, have vasodilatory and anti-platelet effects by enhancing cGMP production. SNO-tPA was compared with tPA in cats in which ischemia/reperfusion injuries were induced. Treatment with SNO-tPA lowered the amount of myocardial necrosis and improved preservation of endothelial function, as assessed by relaxation in response to acetylcholine.

Von Willebrand factor is involved in platelet adhesion. A fragment of von Willebrand factor has been found to have a point mutation, where arginine is replaced by cysteine, and thus can be nitrosated. The fragment itself has anti-platelet properties, but nitrosation improves its ability to inhibit platelet aggregation and adhesion, both in vitro and in an ex vivo rabbit model. All of these effects were mediated both by enhancement of cGMP levels and by decreased binding to glycoprotein (Gp)Ib receptors.

Platelets play a significant role in both the development and the clinical presentation of vascular disease. Currently available agents that reduce platelet activation and adhesion, including aspirin, copidogrel, and abciximab, result in improved outcomes in patients with acute coronary syndromes. However, absolute levels of morbidity and mortality remain high. All RSNOs have been shown to influence platelet function. cGMP is involved in the anti-platelet effects of RSNOs, but, for GSNO, at least, other mediators also appear to be involved. Unlike organic nitrates, which can also lower platelet activity, but at high doses, RSNOs can achieve this in healthy human volunteers in doses that do not affect vascular tone.

Platelet activation, as measured by levels of expression of the adhesion molecule P-selectin and the GpIIb/IIIa receptor, is increased in acute coronary syndromes. This phenomenon is seen even in the presence of aspirin. In a small clinical trial, it was found that GSNO significantly lowered levels of platelet activity. Glyceryl trinitrate also achieved this effect but, because it also induced hypotension, it was less well tolerated.

Interventional treatment of vascular disease using balloon angioplasty and stenting or coronary artery bypass grafting results in platelet activation. This is thought to play a role in the re-stenitic process observed following percutaneous intervention and in graft failure after surgery. SNO-albumin delivered locally to an area of balloon-injured rabbit femoral artery reduced platelet deposition and the subsequent development of neointimal hyperplasia. Local delivery of SNO-albumin using stent-based rather than catheter-based therapy was also found to reduce platelet adhesion following deployment into pig carotid arteries. In a small clinical study, intracoronary infusion of GSNO prior to percutaneous transluminal coronary angioplasty prevented the increases in platelet P-selectin and GpIIb/IIIa expression usually seen within five minutes of the procedure, without altering blood pressure. Coronary artery bypass grafting is also associated with platelet activation and consumption, which can lead to post-operative bleeding. GSNO decreased the uptake of platelets by both arteries and veins in vitro and in patients undergoing coronary artery bypass grafting.

One of the main complications of carotid endarterectonmy is cerebral infarction, often caused by platelet emboli. The procedure itself results in the removal of the endothelium, leaving a potent thrombogenic surface on which platelet adhesion and aggregation occurs. Asymptomatic microemboli can be detected by Doppler ultrasonography, and their frequency correlates with the risk of early stroke. In small studies, intravenous GSNO given either peri-operatively or post-operatively reduced the frequency of microemboli compared with placebo.

Like nitric oxide, RSNOs relax vascular smooth muscle cells. Another therapeutic use for RSNOs is in managing subnarachnoid hemorrhage, a condition associated with cerebral vasospasm. This vascular response was significantly reduced by an infusion of SNAP in a rat model of subarachnoid hemorrhage.

Coronary artery bypass grafting involves the use of both saphenous vein an internal mammary arteries as bypass conduits. Handling of these tissues can include vasospasm, potentially leading to early graft occlusion. Rings of conduit taken from patients undergoing coronary artery bypass grafting were exposed to GSNO and RIG200, another RSNO, and their vascular responses were compared with that seen after exposure to GTN. The RSNOs were found to significantly reduce the degree of vasospasm in these tissue sections compared with GTN.

Reperfusion of ischemic tissue leads to inflammatory responses and endothelial cell dysfunction. RSNOs have been shown to improve end-organ recovery in models of ischemia/reperfusion injury in the heart and the liver.

Thus, RSNOs have many potential roles in the treatment of vascular diseases, limiting the complications of platelet activation, of vasospasm, and of ischemia/reperfusion. These agents may be more effective than currently available nitric oxide donors, such as organic nitrates, which have generally shown little benefit apart from symptomatic relief.

Normal levels of RSNOs detected in bronchoalveolar lavage fluid are approximately 25 μM. RSNOs relax bronchial smooth muscle, inhibiting the broncho-constrictor effects of methacholine on segments of human airway. As with their anti-platelet actions, cGMP appears to mediate only part of this bronchodilatory effect of RSNOs.

Airway RSNO levels are altered in disease states. In patients with pneumonia, the mean concentration was 0.4 μM, higher than that seen in healthy controls. In patients with asthma, nitric oxide levels in exhaled breath are higher than normal, but airway RSNO levels are much reduced as compared with healthy controls.

Like nitric oxide, RSNOs appear to play a role in host defense, affecting both bacteria and viruses. Macrophages produce nitric oxide from L-arginine to exert a cytostatic effect in limiting the complications of platelet activation, of vasospasm, and of ischemia/reperfusion. These agents may be more effective than currently available nitric oxide donors, such as organic nitrates, which have generally shown little benefit apart from symptomatic relief.

Normal levels of RSNOs detected in bronchoalveolar lavage fluid are approximately 25 μM. RSNOs relax bronchial smooth muscle, inhibiting the broncho-constrictor effects of methacholine on segments of human airway. As with their anti-platelet actions, cGMP appears to mediate only part of this bronchodilatory effect of RSNOs.

Airway RSNO levels are altered in disease states. In patients with pneumonia, the mean concentration was 0.4 μM, which was higher than that seen in healthy controls. In patients with asthma, nitric oxide levels in exhaled breath are higher than normal, but airway RSNO levels are much reduced as compared with healthy controls.

Like nitric oxide, RSNOs appear to play a role in host defense, affecting both bacteria and viruses. Macrophages produce nitric oxide from L-arginine to exert a cytostatic effect on *Trypanosoma musculi*. This effect is not seen in the absence of albumin, or in the presence of antibodies to SNO-cysteine, suggesting that the nitric oxide reacts with albumin to form SNO-albumin and then a trans-nitrosation reaction with cysteine occurs to form SNO-cysteine, the active moiety. RSNOs are toxic to a mutant form of *Salmonella typhimurium* in which intracellular homocysteine levels are depleted.

Both nitric oxide and SNAP inhibit HIV-1 protease, an enzyme involved in the replication of this virus. When nitric oxide reacts with the enzyme, it forms nitrosothiols with the two cysteine residues in the protein molecule. This effect on HIV-1 is cGMP-independent and additive with that of zidovudine.

GSNO, SNAP, and SNO-captopril inactivate a protease enzyme in the human rhinovirus, which causes the common cold. This effect probably involves a transnitrosation reaction.

Accordingly, RSNOs can be used to treat conditions ranging from the common cold to AIDS.

RSNOs are inhibitors of gastrointestinal smooth muscle function. Their formation in the gut is thought to occur directly as a result of nitrosation of SH groups of low-molecular-mass thiols. Inhibition of motor activity in the duodenum and sphincter of Oddi is a goal during endoscopic retrograde cholangio-pancreatography. Systemically administered GTN has been shown previously to lower basal tone in the sphincter of Oddi during such procedures, although its use is limited by the development of systemic hypotension. Topical application of S-nitroso-N-acetylcysteine to the ampulla and peri-ampullary duodenal mucosa of humans undergoing endoscopic retrograde cholangio-pancreatoraphy caused a reduction in the frequency of sphincter contractions and in duodenal motility, without a fall in blood pressure, thus facilitating cannulation.

GNSO has been shown to inhibit DNA synthesis and to increase cGMP production by activated T lymphocytes, thus suggesting a role in the prevention of T-cell mediated inflammation. GNSO also has a cytotoxic effect on leukemia cells. Irradiation of GNSO with visible light (340 or 545 nm) resulted in enhancement of this effect, and oxyhemoglobin, a nitric oxide scavenger, decreased it.

Because of their wide range of effects, RSNOs have great potential as therapeutic agents. However, interactions with copper, thiols, ascorbic acid, and other reducing agents influences their stability and ability to act as useful therapeutic agents.

Nitric oxide is unable to react with nucleophiles such as SH groups under oxygen-free conditions, implying that metabolites of NO oxidation, such as $N_2O_3$, are the actual nitrosating agents (Wink et al., 1994; Lewis et al., 1994; Kharitonov et al., 1995; Williams, 1997). However, considering the low concentration and short life span of NO in vivo (t1/2~0.1 s) (Williams, 2001), the third order reaction of NO with oxygen (Moncada et al., 1993), ($k=6\times10^6$ M−2 sec−1) (Wink et al., 1994; Lewis et al., 1994) seems to be too slow to account for any detectable amount of circulating S-nitrosothiols. The high instability of $N_2O_3$ in aqueous solution (Stamler et al., 1992) further supports this notion.

Recently, these apparent theoretical constraints have been resolved by the demonstration of remarkable properties of NO in multi-phase systems (Rafikova et al., 2002; Nedospasov et al., 2000). NO and $O_2$ are both hydrophobic molecules that are more soluble in lipophilic solvents than in water, with a partition coefficient Q in each case >>1. Areas of high hydrophobicity act as a sponge to increase the local concentration of NO and $O_2$ by sequestering them from the surrounding aqueous phase. Under aerobic conditions, high local concentrations of NO and $O_2$ in the hydrophobic phase, e.g., within lipid membranes, can significantly accelerate NO oxidation and $N_2O_3$ formation (Nedospasov et al., 2000; Liu et al., 1998; Goss et al., 1999). This process, known as micellar catalysis, must play a crucial role in NO biochemistry (see FIG. 1).

Body fluids and tissues represent a complex multiphase system where distribution of free NO and $O_2$ and the rate of formation of nitrosating species ($N_2O_3$) should depend on the size and geometry of the hydrophobic phases. Other than lipid membranes, there are many substances that form hydrophobic micelles in vivo, e.g., cholesterol, fatty acids, and hydrophobic cores of protein molecules, with a different Q in each case. Recently, it has been demonstrated that micellar catalysis of NO oxidation is mediated by serum albumin, which has a $Q_{NO}$~120 (Nedospasov et al., 2000). Albumin is the most abundant transport and depot protein in the circulation. Since the concentration of albumin in plasma is large (~800 μM), its hydrophobic core serves as a major absorber of free NO and a catalyst of $N_2O_3$ (Nedospasov et al., 2000). This view is further supported by data which demonstrate that albumin is an efficient catalyst of nitrosation of its own $Cys^{34}$ and $Trp^{230}$ (Nedospasov et al., 2000) as well as circulating low molecular weight RSH (Rafikova et al., 2002).

Since S-nitrosothiols compounds are potent vasodilators and antiplatelet agents, they are considered to be promising therapeutics for a variety of acute and chronic conditions (Hogg, 2000; Al-Sa'doni et al., 2000; Richardson et al., 2002). Understanding the principles of S-nitrosothiol formation in vivo makes it possible to design new approaches to regulate blood flow and clotting and other processes dependent upon nitric oxide. One such an approach is the use of a synthetic hydrophobic phase, such as perfluorocarbons, for the catalysis of NO oxidation and nitrosothiols formation.

Perfluorocarbons are chemically inert, synthetic hydrophobic molecules that possess a unique capability for dissolving a variety of gases, including $O_2$, $CO_2$, and NO. Most therapeutic uses of fluorocarbons are related to the remarkable oxygen-carrying capacity of these compounds. One commercial biomedical perfluorocarbon emulsion, Fluosol (Green Cross Corp., Osaka, Japan) is presently used as a gas carrier to oxygenate the myocardium during percutaneous transluminal coronary angioplasty. Perfluorocarbon emulsions have also been used in diagnostic applications such as imaging.

SUMMARY OF THE INVENTION

It is an object of the present invention to overcome the aforesaid deficiencies in the prior art.

It is another object of the present invention to control nitric oxide metabolism by administering perfluorocarbons.

It is yet another object of the present invention to inhibit nitric oxide activity by administering perfluorocarbons and treat conditions associated with nitrosative stress.

It is yet another object of the present invention to form S-nitrosothiols in vivo for treating a variety of conditions.

It is a further object of the present invention to catalyze NO oxidation in vivo.

It is another object of the present invention to potentiate NO donors formation by administering perfluorocarbons, either alone or in combination with a nucleophile.

It is a further object of the present invention to treat acute hypotension and vasoplegia, particularly when associated with septic shock.

It is another object of the present invention to induce vasorelaxation.

It is still a further object of the present invention to provide antiplatelet effects.

It is another object of the present invention to protect against myocardial ischemic-reperfusion injury.

It is a further object of the present invention to prevent and treat osteoporosis.

It is another object of the present invention to treat diseases and conditions which are affected by the production or inhibition of nitric oxide, including, but not limited to, cardiovascular diseases, respiratory diseases, microbial infections, viral infections, and gastric diseases.

It is a further object of the preset invention to treat diseases and conditions which are mediated by cGMP.

It is another object of the present invention to generate S-nitrosothiols in vivo to treat diseases and conditions which are mediated by cGMP.

It is still another object of the present invention to generate S-nitrosothiols in vivo to treat the cardiovascular system, to influence platelet function, to inhibit vasospasm and ischemia/reperfusion injury, to inhibit pre-eclampsia, to treat respiratory disease by inhibiting broncho-constrictor effects, to reduce frequency in sphincter contractions and improve duodenal motility, to inhibit DNA synthesis and to increase cGMP production by activated T lymphocytes.

It is another object of the preset invention to generate S-nitrosothiols in vivo to treat bacterial and viral infections, including the common cold and HIV.

According to the present invention, perfluorocarbons are used to regulate nitric oxide bioactivity. By controlling nitric oxide bioactivity by administering perfluorocarbons, to avoid either an overabundance or deficiency of nitric oxide, it is possible to control a great number of physiological processes and thus treat or prevent many disease conditions. For example, sequestration of circulating nitric oxide by about 1% w/v perfluorocarbons leads to rapid and potent increase of systemic blood pressure. This property of fluorocarbons can be used to treat acute hypotension and vasoplegia, particularly in septic shock. Alternatively, administration of small amounts (less than about 0.5% w/v) of perfluorocarbons potentiates nitric oxide activity due to acceleration of NO oxidation and NO-donor formation.

Since nitric oxide contributes to the pathogenesis of a number of diseases, including hypertension, atherosclerosis, and diabetes, control of nitric oxide bioactivity enables one to treat these diseases.

To inhibit nitric oxide activity, perfluorocarbons are administered in amounts of at least about 0.5% w/v of total blood, or more. To potentiate nitric oxide activity, perfluorocarbons are administered in amount of less than about 0.5% w/v of blood. To enhance nitric oxide even further, a nucleophile is administered in conjunction with or shortly before or after administration of the perfluorocarbon. Additionally, the patient is irradiated with light of a visible wavelength.

For example, sequestration of circulating nitric oxide by ~0.7% w/v perfluorocarbons leads to rapid and potent increase of systemic blood pressure (FIG. 4). This property of perfluorocarbons can be used to treat acute hypotension and vasoplegia, particularly in septic shock.

Thus, according to the present invention, any disease or condition caused by an excess or a deficiency of nitric oxide can be treated by administering the appropriate amount of perfluorocarbon.

Regulating the activity of NO by administering perfluorocarbons is used to control vascular tone and blood pressure, including pregnancy-induced hypertension (preeclampsia). This is important both for humans and livestock.

Since nitric oxide is a transduction mechanism for steroid hormones, regulation of nitric oxide oxidation by administering perfluorocarbons can be used to regulate estrogen and/or progesterone-dependent steps in reproduction and health of females, including ovulation, implantation, menstruation, climacterium, etc.

Nitric oxide is a potent inhibitor of blood coagulation, and potentiation of nitric oxide activity by administering perfluorocarbons can be used to prevent clotting in the circulation.

Regulating nitric oxide oxidation by administering perfluorocarbons can be used to reduce the incidence and severity of cardiovascular disease, including pathophysiological changes in blood vessels in cardiovascular diseases associated with hypertension and atherosclerosis. Administration of perfluorocarbons to postmenopausal women in addition to or instead of hormone replacement therapy can be used to prevent cardiovascular diseases.

Administering perfluorocarbons to regulate nitric oxide activity can also be used to treat osteoporosis, Paget bone disease, and rheumatoid arthritis by regulating perturbations in the interactions between local and systemic bone-remodeling regulatory pathways.

DETAILED DESCRIPTION OF THE INVENTION

Figure 1:
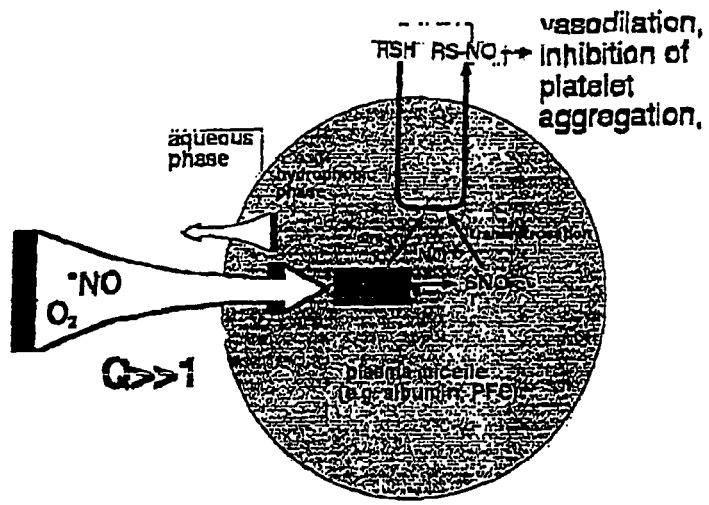
FIG. 1 illustrates micellar catalysis of NO oxidation and S-nitrosation.
Figure 2:
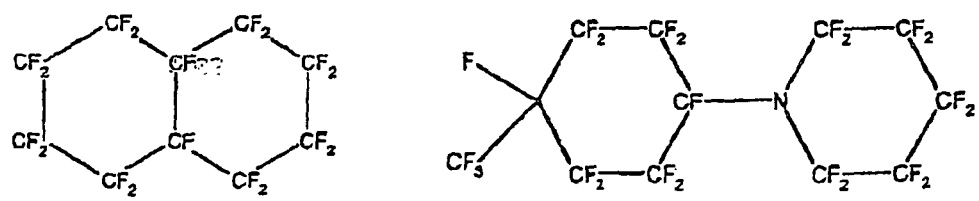
FIG. 2 shows the perfluorocarbon components of Perftoran, perfluorodecaline, and perfluoromethylcyclopiperidine.

The present invention provides a method for regulating nitric oxide oxidation by administering perfluorocarbons. Perfluorocarbons are powerful modulators of nitric oxide activity in mammals, including humans, and thus can be used to treat any disease or disorder that is affected by nitric oxide activity and/or the level of nitric oxide in the organism.

At low levels, when perfluorocarbons are used as a catalyst of nitric oxide oxidation, the effect of the perfluorocarbons is greatly enhanced by the addition of nucleophiles, such as natural or synthetic thiols, which react with the oxidized form of NO and subsequently donate nitric oxide. These nucleophiles can be administered contemporaneously with the perfluorocarbons, before administration of the perfluorocarbons, or after administration of the perfluorocarbons.

Regulating nitric oxide oxidation can be used for treating the following conditions, which are listed for purposes of illustration and not for limitation:

Cardiovascular conditions, including hypertension, angina, hypotension, atherosclerosis, preeclampsia (pregnancy induced hypertension, toxemia, eclampsia, HELP syndrome), regulation of vascular conductance, regulation of blood flow, regulation of blood pressure, and myocardial ischemia;

Gastrointestinal disease, to alter motility and to treat pyloric stenosis;

Lung functions including asthma, treatment of premature babies to increase lung function, and pulmonary hypertension;

Inflammation, autoimmune and immune diseases and conditions including acute inflammation, arthritis, resistance to infection, cancer, lupus, anaphylactic reactions, and allograft rejections;

Central nervous system conditions, including behavior, epilepsy, Alzheimer's disease, stroke, and growth hormone disorders such as acromegaly;

Diseases of the pancreas, including diabetes;

Female reproductive systems or problems, including ovulation, implantation/in vitro fertilization, premenstrual syndrome, dysmenorrhea, uterine contractile disorders, premature labor, cervical dilation, contraception, symptoms of menopause, osteoporosis, endocrine disorder, and hormone replacement;

Male reproductive problems such as impotence, penile erection, symptoms of male menopause, endocrine disorders, osteoporosis, and prostate hypertrophy;

Bladder and kidney problems, including incontinence, renal arterial stenosis, hypertension;

Dermatological problems, including topical hair loss, eczema, autoimmune skin disease, and psoriasis. Additionally, perfluorocarbons are administered to produce S-nitrosothiols in vivo to treat bacterial and viral infections including the common cold and HIV infection.

In the studies described hereinbelow, the perfluorocarbon used was a clinically approved perfluorocarbon emulsion, Perftoran (Perftoran, Inc, Russia). Perftoran contains 14% w/v/perfluorodecaline and 6% w/v perfluoromethylcyclopiperidine that form ~0.07 micrometer micelles which are stabilized by a poloxamer-type surfactant (Sahn, 1999). For convenience, the concentration of perfluorocarbon in all experiments is indicated as % of Perftoran emulsion in the total volume of blood or buffer (v/v).

Perfluorocarbons (PFC) as NO Absorbent and Catalyst of NO Oxidation

The maximum acceleration value (H) of NO oxidation by the hydrophobic phase of Perftoran was calculated by first determining the partition coefficient $Q_{NO}$ ($Q_{NO}=[NO]_{PFC}/[NO]_{H_2O}$) for a PFC/$H_2O$ system. A Clark-type NO electrode (WPI Inc.) was used to monitor changes in the NO concentration in water upon addition of PFC in an air-tight oxygen-free device. Oxygen was removed from water and Perftoran prior to the experiment by bubbling each of Perftoran and water with argon for 12 hours. The $Q_{NO}$(PFC/$H_2O$) was found to be approximately 200. $Q_{O_2}$(PFC/$H_2O$) was found previously to be about 20 (Gervits, 1994).

For the tri-molecular reaction of $N_2O_3$ formation, $H=Q^2_{NO} \times Q_{O_2}=200^2 \times 10 = 4 \times 10^5$. This result suggests that even a small amount (1% v/v) of perfluorocarbon emulsion in mammalian blood should sequester a significant amount of circulating NO. At the same time it should accelerate the production of vasoactive NO metabolites, such as S-nitrosothiols, due to micellar catalysis of NO oxidation. These S-nitrosothiols can be created in vivo for treatment of a wide variety of diseases and conditions, as described above.

Stimulating Effect of Perfluorocarbon on the Formation of S-nitrosothiols

Figure 3B:
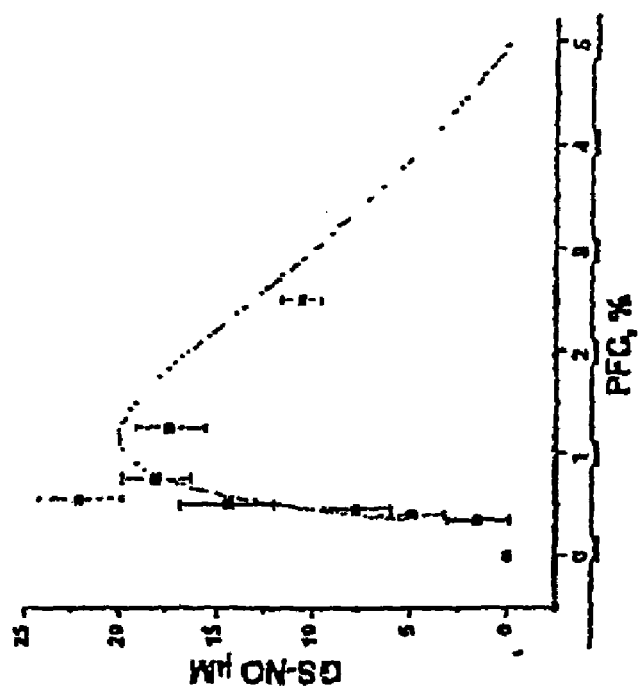
FIG. 3B shows perfluorocarbon-mediated generation of GS-NO as a function of the volume of the hydrophobic phase (% v/v Perftoran). Low molecular weight S-nitrosothiols were determined using $CuCl_2$ to displace NO from thio residues followed by electrochemical detection of released NO (Rafikova et al., 2002).
Figure 3A:
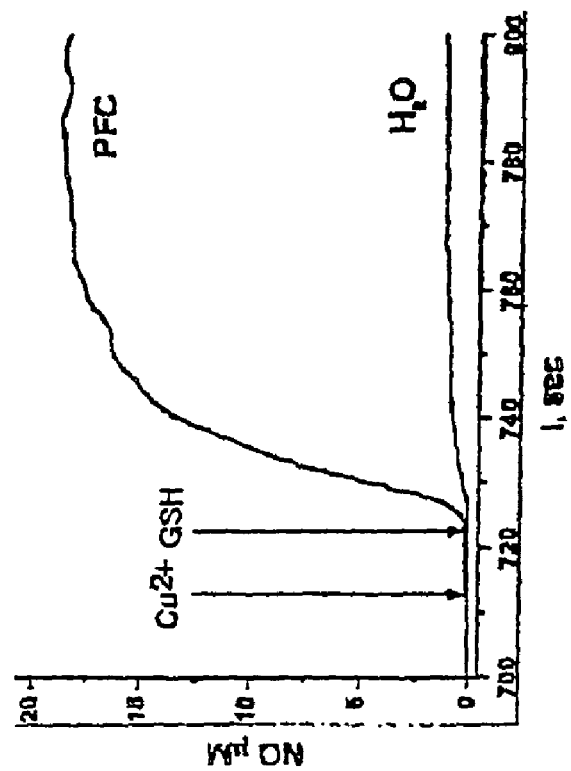
FIG. 3A shows a representative NO-electrode tracing of $Cu^{2+}$-dependent NO production after an addition of 1 mM GSH to 1% v/v Perftoran (PFC tracing) or control (Tris-HCl buffer [80 mM, pH 7.9] (buffer tracing). Bolus NO (100 µM water solution) was added to Perftoran or buffer prior to GSH addition. As soon as the concentration of NO in each probe dropped to less than 1 µM, as detected electrochemically, GSH was added.

A representative experiment, illustrated in FIG. 3A, shows that 1% v/v perfluorocarbon that was saturated with NO (0.5 µM final concentration) increases the rate of S-nitroso-glutathione (GS-NO) formation more than 20-fold in vitro. Under similar conditions, perfluorocarbon was also shown to accelerate S-NO-cysteine, S-NO-homocysteine, and nitrite formation. The relative stimulating effect of perfluorocarbons on GSH nitrosation was even greater at the lower, close to in vivo, concentration of NO. Importantly, the efficiency of perfluorocarbon-mediated S-nitrosation also depended upon the amount of perfluorocarbon in the probe, as shown in FIG. 3B. The resonance-like maximum was observed at about 1% v/v Perftoran. Larger or smaller amounts of perfluorocarbon were progressively less efficient. This observation is readily explained in terms of micellar catalysis of NO oxidation, when the relatively small "optimal" volume of the hydrophobic phase (in this case perfluorocarbon) generates the maximum acceleration of the reaction (Rafikova et al., 2002; Beda et al., 1999). These results suggest that by using various amounts of perfluorocarbon together with low molecular weight nucleophiles, one can regulate the level of endogenous vasoactive low molecular weight S-nitrosothiols. Notably, uncoupling NO-donors formation from overall NO synthesis not only provides a new way to control blood pressure and organ perfusion, but also creates a unique opportunity to relieve the nitrosative stress (excessive nitration and nitrosation of proteins and nucleic acids) during inflammation (Poli, 2002; Beckman et al., 1996; Beckman et al., 1994). Thus, perfluorocarbons can be administered to regulate blood pressure and blood clotting. Studies in humans and animals have shown that the body retention half-life of Perftoran is about 48 hours (Lowe, 1999).

Perfluorocarbon as a Powerful NO Sink In Vivo and Catalyst of S-nitrosothiols

Figures 4A, 4B:
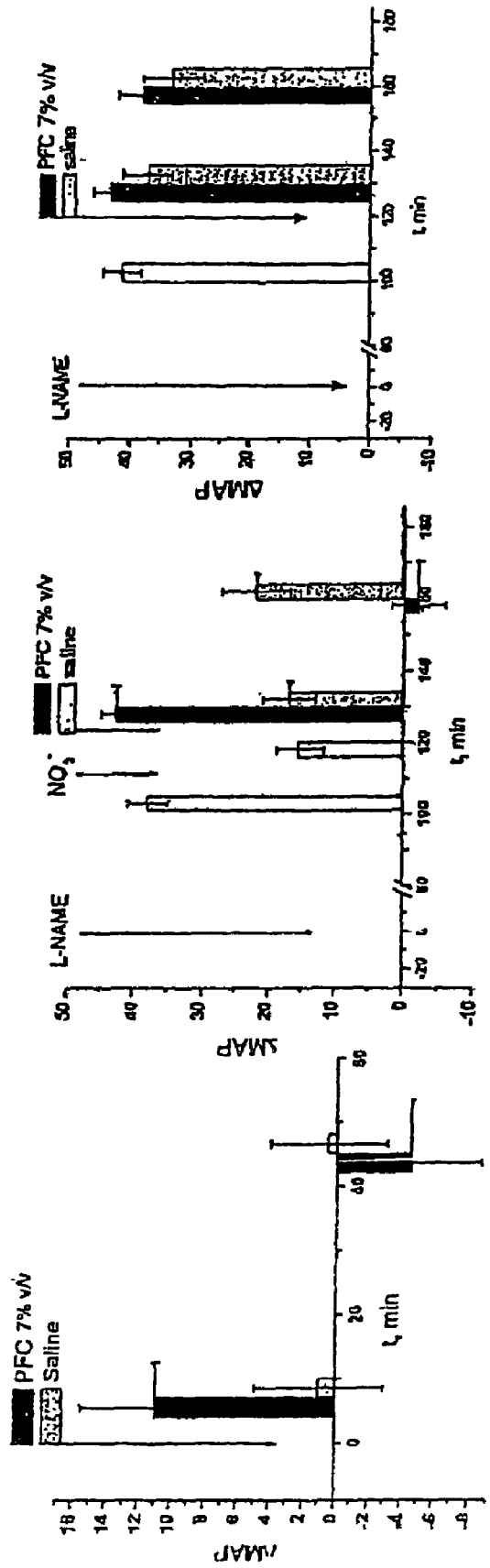
FIG. 4A shows the effect of the "high dose" (7% v/v) of perfluorocarbon on mean arterial pressure of anesthetized rats.
FIG. 4B shows the relation of perfluorocarbon-mediated hemodynamic effects to NO.

The effect of Perftoran on mean arterial pressure (MAP) in rats was studied to evaluate the ability of perfluorocarbon micelles to absorb circulating NO in vivo, and the physiological role of this phenomenon. Intravenous perfusion of 5 ml/kg (~7% v/v) Perftoran was characterized by extensive hypertension, as shown in FIG. 4A. It should be noted that the solution of perfluorocarbon that was used was isooncotic. Also, the amount of Perftoran was only about 0.7% w/v of total blood, and the rate of its infusion was slow (0.2 ml/min). This rules out the possibility that perfluorocarbon affected mean arterial pressure by changing the osmotic status.

In FIG. 4A, infusion of 5 ml/kg Perftoran produced a steep increase in blood pressure (11±4 mm Hg), followed by a gradual asymptotic recovery. Delivery of Perftoran or saline intravenously was at a constant rate of 0.2 ml/min with an electronic perfusator. The mean±SE was obtained from 111 independent experiments.

To confirm that the increase of blood pressure by perfluorocarbons was due to NO sequestration, the following experiment was conducted, as illustrated in FIG. 4B. First, the experimental group of animals received a non-selective NOS inhibitor, N-nitro-L-arginine methyl ester (L-NAME, 50 mg/kg, intraperitoneally) to deplete the vasculature of endogenous NO, thus causing a characteristic increase of mean arterial pressure, as shown in FIG. 4B. Perftoran failed to increase mean arterial pressure further, as shown in the right panel of FIG. 4B, suggesting that endogenous NO was essential for perfluorocarbon-induced vasoconstriction. Furthermore, the infusion of 1 mg/kg potassium nitrite about 90 minutes after the L-NAME treatment partially restored mean arterial pressure, as shown in FIG. 4B. In this case, administration of Perftoran elevated mean arterial pressure back to the original L-NAME level, as shown in FIG. 4B. The nitrite was readily reduced to NO in vivo, which explains its vasorelaxation effect. The ability of Perftoran to effectively reverse the nitrite effect on mean arterial pressure confirmed its mode of action as a powerful NO sink.

It was noted that about 30 minutes after infusion of Perftoran, nitrite-treated rats exhibited a much stronger decrease of mean arterial pressure (mean arterial pressure dropped to the original baseline level) than the control group without Perftoran (mean arterial pressure remained about 24 mmHg above the baseline, as shown in FIG. 4B).

Also, a modest but reproducible delayed decrease of mean arterial pressure by perfluorocarbons was observed in the experiment without nitrite and L-NAME, shown in FIG. 4A. These results can be interpreted as that, during the first phase of action, perfluorocarbon rapidly adsorbs NO, causing the initial increase of mean arterial pressure. However, since the local concentration of NO and $O_2$ in perfluorocarbon micelles becomes high, the nitrosating species ($N_2O_3$) form as a result of accelerated NO oxidation. This process, in turn, leads to vasoactive S-nitrosothiols formulation, shown in FIG. 3, and vasorelaxation. The experiment shown in FIG. 5 supports this hypothesis. Here, animals received 10 times less Perftoran intravenously than in the experiment shown in FIG. 4. Although the initial jump of mean arterial pressure was not as dramatic, a subsequent drop in mean arterial pressure was significantly more rapid and pronounced (compare FIG. 5 with FIG. 4A). The reasonable explanation for such a reverse dose-dependent effect of perfluorocarbon on blood pressure originates from the micellar catalytic nature of PCF/NO interactions. As mentioned above, the theory of micellar catalysis states that there should be an optimal volume of a hydrophobic phase, in this case perfluorocarbon, to have a maximum stimulating effect on the reaction, in this case oxidation of NO and formation of nitrosating species (Rafikova et al., 2002; Beda, et al., 1999). Indeed, according to FIG. 3B, about 1 v/v % Perftoran generated the highest yield of S-nitrosothiols. Larger or smaller amounts of perfluorocarbon are progressively less efficient. Assuming that Perftoran catalyzes formation of S-nitrosothiols in vivo, this dose-dependent vasodilatory effect is expected to reflect the dose-dependent curve of Perftoran-mediated S-nitrosothiols formation in vitro (FIG. 3B). Accordingly, 1% v/v perfluorocarbon (FIG. 5) relaxes vascular tone more efficiently that 7% v/v perfluorocarbon (FIG. 4A).

Figure 6B:
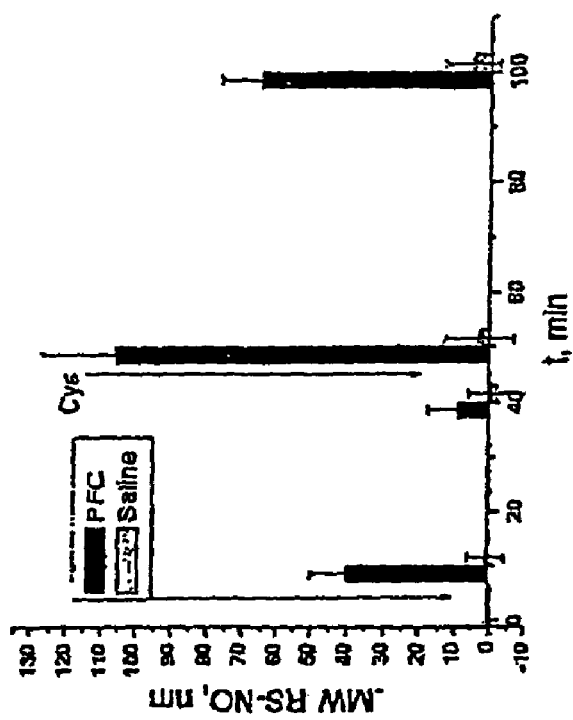
FIG. 6B shows the change in plasma low molecular weight nitrosothiols in response to perfluorocarbons and cysteine.

To directly demonstrate the ability of perfluorocarbons to catalyze S-nitrosothiol formation in vivo and to confirm its relation to perfluorocarbon-induced vasorelaxation, measurements of mean arterial pressure were conducted in parallel with direct monitoring low molecular weight-S-nitrosothiols in plasma before and after Perftoran administration, as shown in FIG. 6. Plasma low molecular weight-S-nitrosothiols were determined using $CuCl_2$ to displace NO from thiol residues followed by electrochemical detection of released NO (Rafikova et al., 2002). The concentration of $CuCl_2$, 40 µM, was selected to decompose predominantly low molecular weight S-nitrosothiols. The relatively stable high molecular weight S-nitrosothiols (e.g., S-NO-albumin) were mostly resistant to such low concentrations of $Cu^{2+}$ (unpublished observation). As FIG. 6B shows, the level of plasma low molecular weight S-nitrosothiols increased by about 40 nM (about 10-fold) after 10 minutes of 1% v/v Perftoran injection, and then gradually decreased over the next hour.

Figure 5:
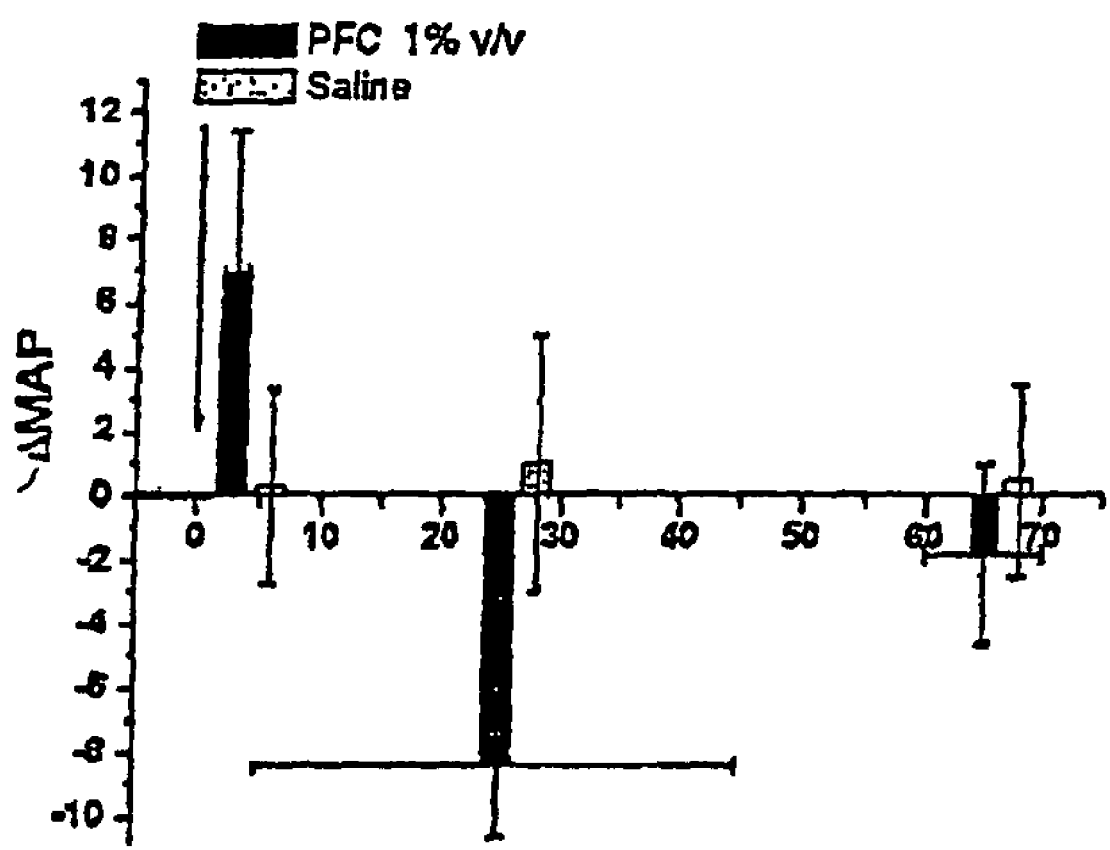
FIG. 5 shows the effect of the administration of the "low dose" (1% v/v) of perfluorocarbon on mean arterial pressure.
Figure 6A:
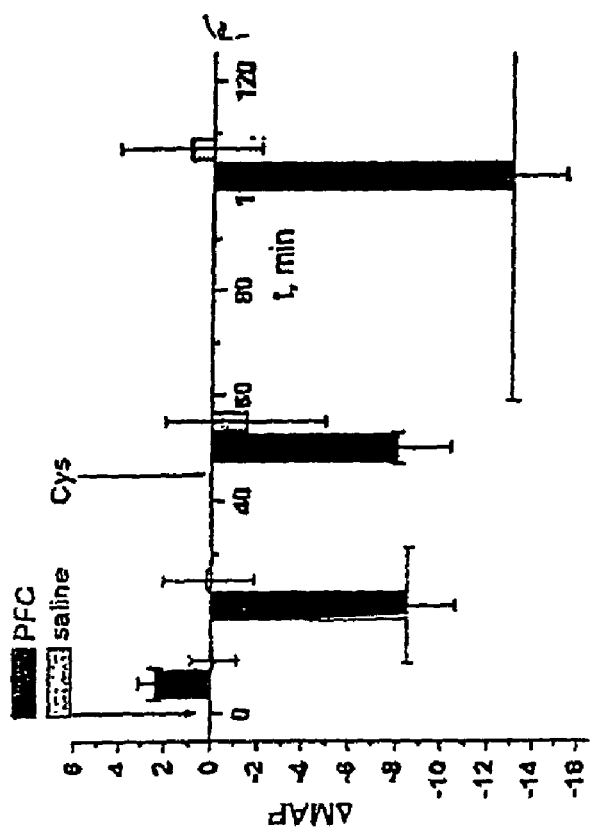
FIG. 6A shows the combined effect of perfluorocarbons and thiols (L-cysteine) on mean arterial pressure.

To confirm that induced vasorelaxation was due to S-nitrosothiols formation, the effect of exogenous molecular weight thiols on mean arterial pressure and S-nitrosothiols formation was studied in perfluorocarbon treated animals. Without perfluorocarbon, cysteine (1 mg/kg, intravenously) had virtually no effect on plasma low molecular weight S-nitrosothiols or on blood pressure, as shown in FIG. 6. However, in the PFC-pretreated rats, the same amount of cysteine caused more than 100 fold increase of plasma low molecular weight S-nitrosothiols (FIG. 6B), and significant decrease of mean arterial pressure (FIG. 6A). The decrease of mean arterial pressure due to the combined effect of perfluorocarbon and cysteine was much stronger than that of perfluorocarbon alone (compare FIG. 5 with FIG. 6A). Similar vasorelaxation effects and stimulation of S-nitrosothiols formation were observed when another low molecular weight thiol, GSH, was administered to perfluorocarbon pretreated rats instead of cysteine. Taken together, the results obtained demonstrate that perfluorocarbons can preserve otherwise unstable circulating NO in a form of more stable vasoactive low molecular weight S-nitrosothiols, which explains the hemodynamic effects of perfluorocarbons.

The unique ability of perfluorocarbons to control NO bioactivity can be used to regulate blood pressure and clotting and other NO-dependent processes with minimum side effects that are normally associated with activation/inhibition of NOS. Thus, in order to increase blood flow one can administer >>1% v/v perfluorocarbons to rapidly sequester free circulating NO without compensatory production of S-nitrosothiols due to inefficiency of micellar catalysis of NO oxidation. On the other hand, to decrease blood pressure to a steady level, one can administer about 0.5% or less v/v perfluorocarbon with various low molecular weight nucleophiles. Under these conditions, a relatively small increase in plasma nucleophile, such as low molecular weight thiols, would have a great stimulating effect on vasodilatory S-nitrosothiols production, as shown in FIGS. 6A and 6B. Since perfluorocarbons have a half-life in mammals of from about 24-48 hours, the perfluorocarbons could be administered as infrequently as several times a week.

A common cause of acute inflammation or sepsis are severe bacterial infections that are frequently associated with hospitalized and/or otherwise exhausted individuals in which a standard host defense is compromised. Septic shock is associated with high mortality, and current therapy is mostly supportive and ineffective (Nakazawa et al., 2000; Wenzel, et al., 1996). During septic shock, systemic overproduction of NO by transient early activation of endothelial NOS (eNOS) and a subsequent hyper-induction of inducible NOS (iNOS) is the major cause of acute hypotension and poor organ perfusion (Wenzel et al., 1996; Titheradge, 1999). It also leads to excessive protein and nucleic acid nitration in tissues and body fluids, apparently because of the presence of a high level of $ONOO^-$, a product of the reaction between NO and $O_2$ (Beckman et al., 1996; Beckman et al., 1994; Titheradge, 1999). On the other hand, activation of iNOS in white blood cells is one of the key mechanisms to combating infection (Titheradge, 1999; DeGroote et al., 1999). The unique ability of perfluorocarbons to rapidly sequester circulating NO without suppressing NOS activities makes perfluorocarbons useful in attenuating hypotension and vasoplegia during septic shock. Perfluorocarbon micelles cannot penetrate the cell membrane or diffuse into the tissue, and thus they should not significantly affect the intracellular NO levels, which is required for a potent immune defense (Titheradge, 1999; DeGroote et al., 1999). Furthermore, by decreasing the concentration of circulating NO, perfluorocarbons are expected to subdue the $ONOO^-$ mediated tissue damage. Finally, unlike NOS inhibitors, perfluorocarbon emulsions are not expected to cause excessive vasoconstriction, platelet aggregation, leukocyte adhesion, and many other adverse effects of systemic NO depletion (DeGroote et al., 1999) because of a compensatory production of S-nitrosothiols.

Figure 7:
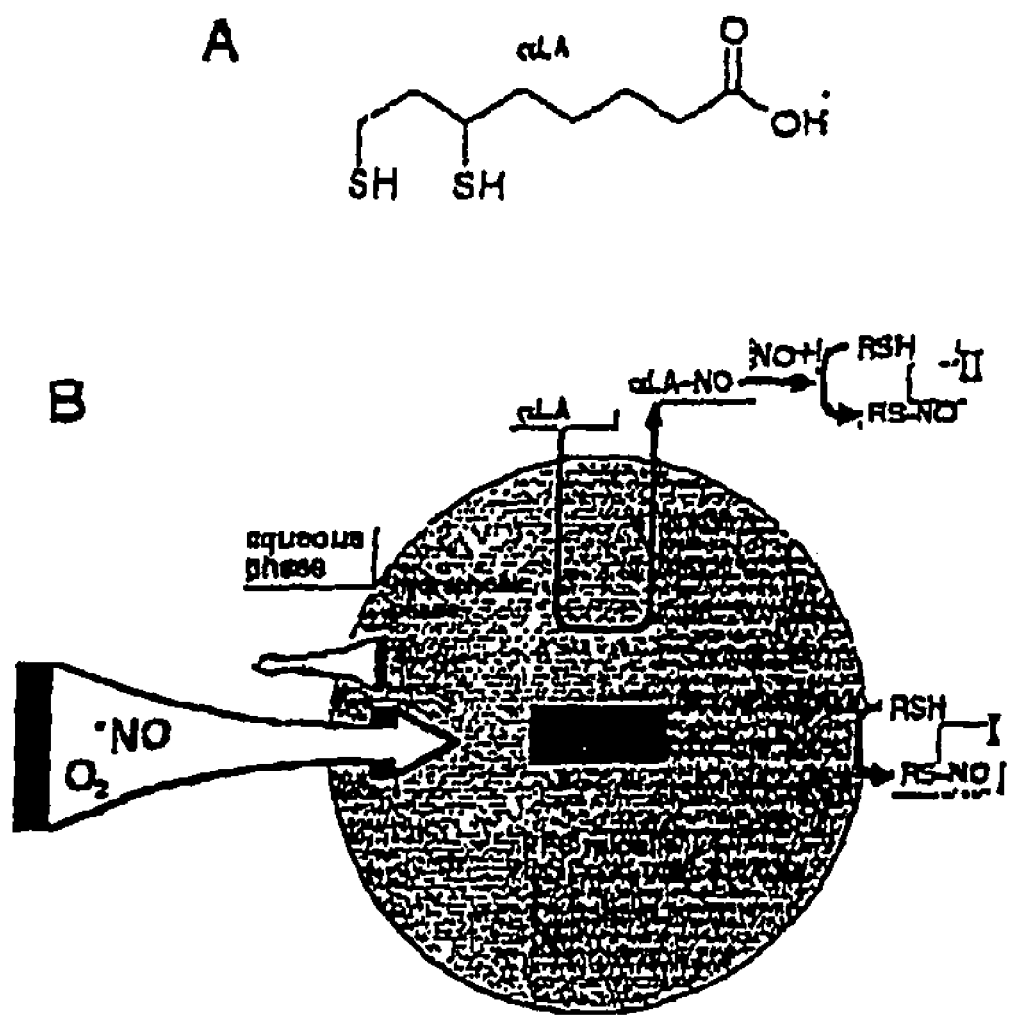
FIG. 7 illustrates the cascade mechanism of nitrosothiols formation mediated by α-lipoic acid.
Figure 8:
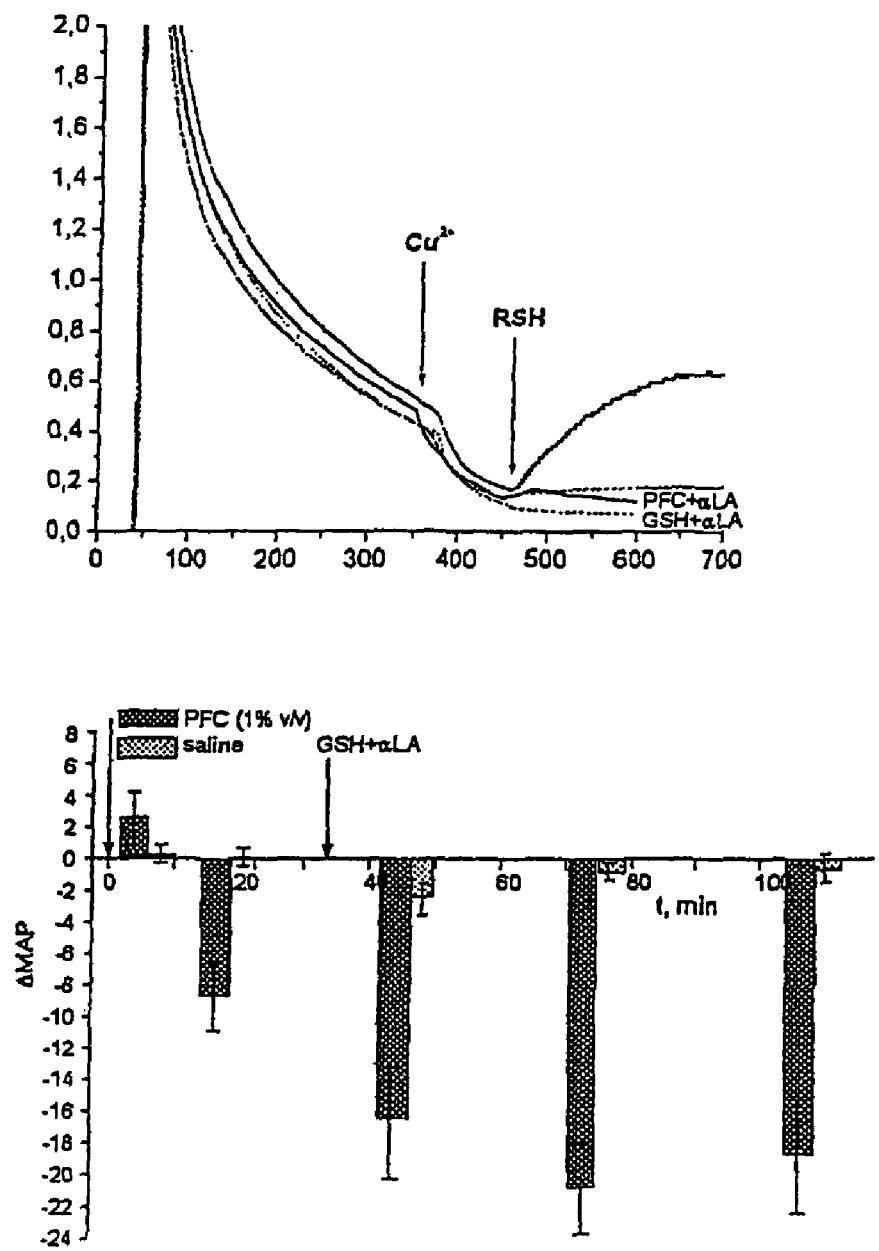
FIG. 8 demonstrates the simulating effect of α-dihydrolipoic acid on the formation of nitrosothiols as well as vasorelaxation in the presence of perfluorocarbons.

If delivered at small concentrations, i.e., less than 1% v/v, and in conjunction with low molecular weight nucleophiles, such as thiols or mixtures of thiols, perfluorocarbons act as a powerful vasodilator rather than as a vasoconstrictor. This effect is due to micellar catalysis of vasoactive S-nitrosothiols formation by perfluorocarbons, as shown in FIGS. 3, 5, and 6. $NO^+$ originated from $N_2O_3$ in the perfluorocarbon micelles can be transferred to various low molecular weight nucleophiles, exemplified as RSH, by two possible pathways, as shown in FIG. 7. Direct attack on RSH is possible at the surface of perfluorocarbon micelles or inside the micelles, if the RSH were hydrophobic enough to enter it, as shown in pathway I of FIG. 7. Additionally, NO can reach various RSH via a transnitrosation reaction by using a lipophilic low molecular weight "shuttle", as shown in FIG. 7. One example of such an NO shuttle is α-lipoic acid (α-LA), which is normally present in the circulation at low (micromolar) concentrations (Keipert, 2001). α-lipoic acid has a highly hydrophobic tail (FIG. 7A), which can readily penetrate the perfluorocarbon micelle where it is nitrosated. Since both SH groups of α-dihydro-lipoic acid are located next to each other, upon nitrosation they would almost immediately form an S-S adduct and release $NO^+$. Thus, α-lipoic acid may serve as a shuttle to transfer $NO^+$ from the perfluorocarbon micelle interior to outside hydrophilic low molecular weight RSH thus potentiating the PFC-mediated RS-NO formation (FIG. 7B) Our in vitro and in vivo results support this conclusion (FIG. 8). Since low molecular weight S-nitrosothiols are potent vasodilators and anticoagulants, they are regarded as promising cardiovascular therapeutics (Hogg, 2000; Al-Sadoni et al., 2000; Richardson, et al., 2002). However, the major drawback of available low molecular weight S-nitrosothiols is that they are very unstable in physiological vehicles. Moreover, high doses of S-nitrosothiols can be toxic and dangerously affect blood flow. Therefore, the use of stable and safe RSH, such as GSH, cysteine, and α-lipoic acid in conjunction with perfluorocarbons to achieve the same effects as that of corresponding exogenous S-nitrosothiols should be advantageous.

The unique properties of perfluorocarbons as carriers of $O_2$/NO and generators of S-nitrosothiols make them useful in protecting against myocardial ischemic-reperfusion injury. Perfluorocarbon micelles are smaller than red blood cells (e.g., 0.07 micrometer for Perftoran, Loew, 1999; Spahn, 1999), and thus should better overcome vascular occlusion to deliver $O_2$ to ischemic tissue. Many experiments on rabbits and dogs have demonstrated significant reduction of myocardial infarct size by intravenous Fluosol treatment (Timmermans et al., 1993; Forman et al., 1985; Rice et al.). However, subsequent Fluosol experiments with rabbits and human trials with Fluosol failed to demonstrate such a healing effect (Forman et al., 1992; Wall et al., 1994). Fluosol, the only perfluorocarbon approved in the U.S. for angioplastic procedures, has a number of disadvantages in comparison with more advanced perfluorocarbon emulsions such as Perftoran and Oxygent, including larger particle size, lower $O_2$ capacity, higher viscosity, and instability (Lowe, 1999). Most importantly, previous studies have not considered the role of perfluorocarbons as modulators of NO bioactivity.

The well-established cytoprotective action of NO during perfusion-reperfusion (reviewed in Kloner et al., 1994; Hale et al., 1995) and its favorable effects on diastolic dysfunction (Rakhit et al., 2001), often associated with reperfusion injury, provide a rationale for using perfluorocarbons as NO-releasing agent in this context. It has been noted that perfluorocarbons preserve the endothelium and prevent NO-reflow by inhibiting neutrophil function, including adherence to endothelial cells and release of toxic substances (reviewed in Vinten-Johansem et al., 1999). The same function has been attributed to NO in many studies (Hale et al., 1995; Paulus et al., 1994). NO also plays a principal role in delaying ischemic preconditioning, the phenomenon in which a stimulus, which can be brief coronary ischemia, renders the myocardium more resistant against the subsequent sustained ischemia and reperfusion. Generally, the cardioprotective effects of NO against ischemia/reperfusion injury may be achieved directly or indirectly through its well-known biological actions such as coronary vasodilation, reduction of myocardial $O_2$ consumption, and opening of KATP channels (Heard et al., 2000; Yin et al., 1997). Recently, NO releasing substances have been also shown to suppress restenosis after transluminal coronary angioplasty (Miyoshi et al., 1994; Sasaki et al., 2000).

A study was conducted to demonstrate the use of perfluorocarbons in treating endotoxic shock in rats. Male Wistar rats (15 animals per group) weighting 250-300 grams were anesthetized intraperitoneally with 1.2 mg/kg of urethane. The right femoral artery was cannulated with PE50 tubing and connected to a PowerLab pressure transducer for measuring arterial blood pressure. PE50 catheters were placed into the right femoral vein for infusion of various agents.

Figure 10A:
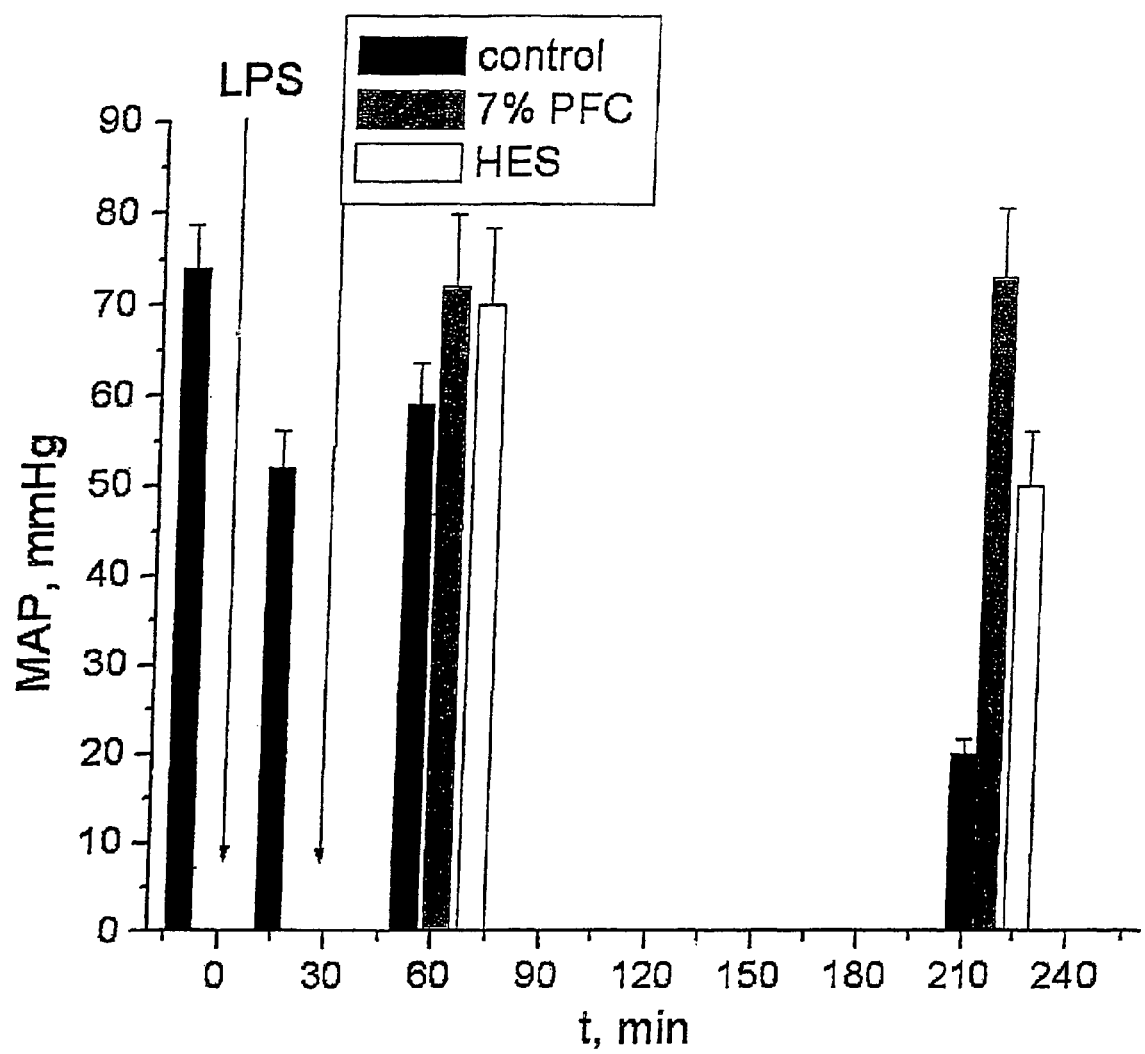
FIGS. 10A and 10B demonstrate the use of perfluorocarbons in treating endotoxic shock.

Sepsis was induced intravenously by a bolus of endotoxin from *Escherichia coli* LPS, 50 mg/kg. The results shown in FIG. 10A demonstrate that a single bolus infusion of perfluorocarbon, 7% v/v, 0.2 ml/min, thirty minutes after administration of LPS improves the hemodynamic by preventing loss of blood pressure. The control treatment was no treatment, and HES was the standard starch treatment. In FIG. 10A, MAP is mean arterial pressure.

Figure 10B:
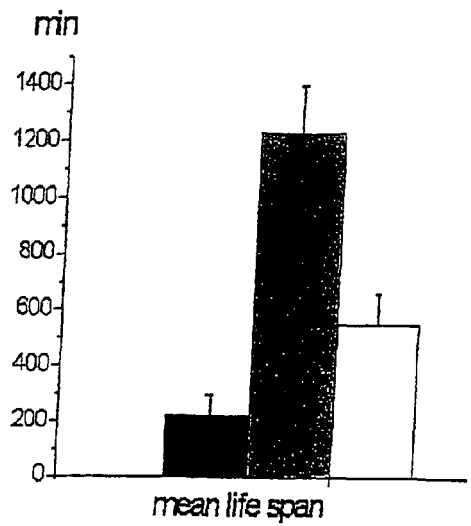

As shown in FIG. 10B, the survival of the animals after 24 hours was increased six-fold in comparison with control and HE S groups, respectively.

In contrast with its cardioprotective actions, NO in larger quantities, such as those normally associated with inflammation and generation of deleterious $ONOO^-$, has also been implicated in promulgating coronary injury (Maffia et al., 2002). For example, L-NAME NOS inhibitor reduced infarct size in an in situ rabbit model (Min et al., 2001), and this cardioprotective effect can be reversed by co-administration of L- but not D-arginine, confirming involvement of the L-arginine NO pathway (Bolli, 2001). In a majority of experiments, however, L-arginine, NO gas, and NO-donors have been shown to protect against reperfusion injury to various degrees (Woolfson et al., 1995; Schulz et al., 1995; Johnson et al., 1991). Evidence suggests that the protective effect, in large part, is due to attenuation of neutrophil-endothelial cell interactions (Hale et al., 1995; Siegfried et al., 1992). Thus, NO levels should be finely balanced in the ischemic tissue to exert its cardioprotection, since a deficiency as well as an excess of NO can lead to further tissue damage. The use of conventional NO-donors has always been associated with two major problems: instability of most such chemicals in physiological vehicles, and their toxicity (Richardson et al., 2002). In this regard, perfluorocarbons/nucleophiles present a much safer pharmacological tool that allows for a sustained and finely regulated delivery of endogenous NO to the ischemic tissue.

To achieve maximum cardioprotection, specific iNOS inhibitors such as S-methylisothiourea or aminoguanidine can be administered together with the nucleophile to minimize excessive production of NO in the vicinity of injury and to spare the regional nitrosative stress. In this case, the major source of NO in the ischemic heart is from S-nitrosothiols that were endogenously formed in perfluorocarbon micelles far from the ischemic zone. As noted previously, low molecular weight S-nitrosothiols have a greater potency than free NO due to their higher stability and specific intracellular transport (Rafikova et al., 2002; Hogg, 2000). At the same time, S-nitrosothiols cannot directly produce $ONOO^-$ and other reactive nitrogen species, thus eliminating the major toxic effects of NO. Finally, the advantage of endogenous low molecular weight S-nitrosothiols is that their levels can be finely and safely regulated simply by changing the concentration and combination of exogenous thiols (FIG. 6).

Ischemic preconditioning is an important aspect of cardioprotection that involves NO and thus can be treated with perfluorocarbon/RSH. Originally described as an immediate adaptation of the heart to brief coronary occlusion (Murry, et al., 1986), ischemic preconditioning was subsequently found to be a biphasic phenomenon, with the early phase of protection that develops within minutes from the initial ischemic insult and lasts 2 to 3 hours, and a late (or delayed) phase that becomes apparent 12 to 24 hours later and lasts for 3 to 4 days (Pabla et al., 1996; Bolli, 2001). Unlike the early phase, the late phase of ischemic preconditioning protects not only against myocardial necrosis and arrhythmias, but also against myocardial stunning (Kuzuya et al., 1993), suggesting that it may have greater clinical relevance. Many independent studies have shown that NO is not only necessary, but also sufficient to induce late ischemic preconditioning (reviewed in Bolli, 2000; Maffia et al., 2002). Furthermore, the critical role of endogenous and exogenous NO in extension of both early and late phases of ischemic preconditioning have been well documented (Maffia et al., 2002; Marber et al., 1993; Bolli, 1996). Thus perfluorocarbon/RSH can be used to produce endogenous low molecular weight S-nitrosothiols for triggering and extending the late phase of ischemic preconditioning against myocardial infarction. The advantage of using endogenous low molecular weight S-nitrosothiols is twofold: 1. S-nitrosothiols are more efficient than NO itself, as discussed above, and 2. unlike NO, S-nitrosothiols cannot sequester oxygen free radicals and form detrimental $ONOO^-$. This is important not only for protection against nitrosative stress and tissue damage by $ONOO^-$, but also for better activation of preconditioning, since the presence of free oxygen radicals has been shown to be essential for ischemic preconditioning cardioprotection (Kuzuya et al., 1993; Xi et al., 2000).

Thus, perfluorocarbon emulsions can be used as synthetic regulators of NO bioactivity in animals, particularly in acute cardiovascular conditions. This is based upon the micellar catalysis of NO oxidation and vasoactive S-nitrosothiols formation that has been established in vitro as well as in vivo (Rafikova et al., 2002; Nedospasov et al., 2000).

The perfluorocarbons are colorless liquids with low viscosity and densities ranging generally from about 1.8 to about 2.0 g/mL. Perfluorocarbons are immiscible with water and with most organic solvents. Therefore, for intravenous administration, the perfluorocarbons must be emulsified with aqueous solutions of electrolytes and buffers, also containing surfactants and oncotic (colloid-osmotic) components. Emulsification is achieved by ultrasonic vibration (sonication) followed by dialysis for removing any traces of toxic fluoride anions formed during sonication, or by high-pressure homogenization, which is more appropriate for large-scale manufacture of emulsions.

One example of a perfluorocarbon emulsion is Fluosol, manufactured in Japan by Green Cross Corporation. Fluosol is a 10% emulsion in injectable water made by combining three separate solutions prior to emulsification and administration as follows:

| Solution 1: | |
| --- | --- |
| Perfluorodecalin | 14.0% w/v |
| Perfluoro-tripropylamine | 6.0 |
| Pluronic-F-68 | 2.7 |
| Yolk phospholipids | 0.4 |
| Glycerol | 0.8 |
| Solution 2: | |

| -continued | |
| --- | --- |
| Potassium chloride | 0.034 |
| Sodium hydrogen carbonate | 0.210 |
| Solution 3: | |
| Sodium chloride | 0.60 |
| Calcium chloride | 0.028 |
| Magnesium chloride | 0.020 |
| Glucose | 0.180 |
| Hydroxyethyl starch | 3.0 |

Other examples of a perfluorocarbon emulsion are Perftoran, manufactured in Russia by Perftoran Inc, and Oxygent, which is made in the U.S. by Alliance Pharmaceuticals Inc.

Other perfluorocarbon emulsions are prepared by starting with pure perfluoro precursors and reacting them with another compound to yield a pure substance. For the optimal trade-off between low volatility, leading to too high retention times in the body, and too high volatility, leading to possible circulation problems, the range of molecular weights of the perfluorocarbons should lie within the limits of about 400-700 Daltons. The optimal particle size of the perfluorocarbon micelles is from about 25 nm to about 1 micron. The surfactants used provide emulsions that have a long shelf life at room temperature in the final sterile emulsion.

The perfluorocarbons of the present invention must be substantially non-toxic and not be significantly metabolized in vivo. They should also be non-immunogenic.

Representative perfluorocarbons which can be used in the present invention to regulate nitric oxide include perfluorinated hydrocarbons such as perfluorinated decalin, perfluorinated adamantine; halogen derivatives such as octyl bromide; tertiary amines such as perfluorinated tributylamine or perfluorinated tripropylamine; nitrogen-containing heterocycles such as perfluorinated N-methyl isoquinoline, perfluorinated N-(4-methylcyclohexyl)-piperidine; and oxygen-containing heterocycles such as perfluorinated 2-n-butyl-tetrahydrofuran. Other examples of highly fluorinated compounds which can be used in the present invention are perfluorooctyl ethane, perfluorohexylethane, 1,2-bis(perfluorobutyl)ethane, and 1,2bis(perfluoroethyl)ethene. Perfluorocarbons are described in, for example, U.S. Pat. Nos. 3,962,439; 3,493,581; 4,110,474; 4,186,253; 4,187,252; 4,252,827; 4,423,077; 4,443,480; 4,534,978; and 4,542,147, the entire contents of each of which are hereby incorporated by reference. For the purposes of the present application, the term "perfluorocarbons" will include all of these types of compounds, as well as mixtures thereof.

The perfluorocarbons generally comprise up to about 70-75% by volume of the emulsions used in the present invention. Preferably, the emulsions of the present invention comprise from about 10% to about 75% by volume of perfluorocarbons, with about 0.5 to about 7.5% (by weight of the non-fluorocarbon volume) of surfactant.

Surfactants for use in the perfluorocarbon emulsions of the present invention include any of the known anionic, cationic, nonionic, and zwitterionic surfactants. Combinations of surfactants can be used in the emulsions, the most important criterion being that the surfactants are non-toxic. Particularly useful surfactants include egg phosphatides, lecithin, and alkyl salts of oleic acid such as sodium oleate.

When the perfluorocarbon is used in low concentrations as a nitric oxide oxidation catalyst, it may be administered with a low molecular weight nucleophile, which greatly enhances the effect of the perfluorocarbon.

The nucleophiles are converted into nitric oxide donors in vivo upon reaction with the oxidized NO species (e.g. $N_2O_3$) inside, or at the surface of, perfluorocarbon micelles (FIG. 1, FIG. 7B). Nitric oxide donors exert stronger physiological effects than free nitric oxide due to a much longer lifetime in vivo.

Figure 9:
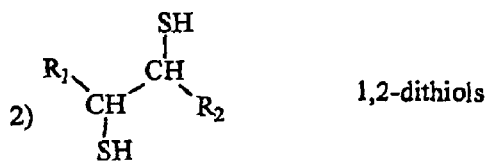
FIG. 9 illustrates small molecule nucleophiles that can be coadministered with perfluorocarbons to potentiate the action of the perfluorocarbons.
Figure 9:
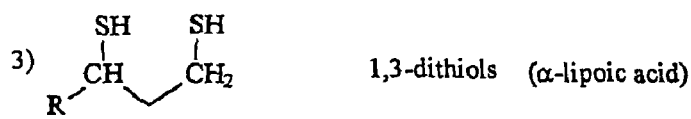
Figure 9:
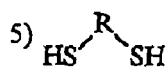
Figure 9:
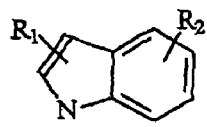
Figure 9:
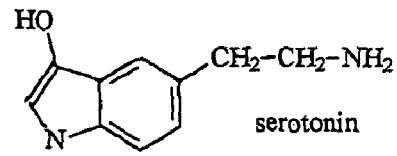
Figure 9:
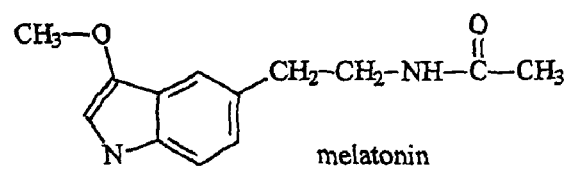
Figure 9:
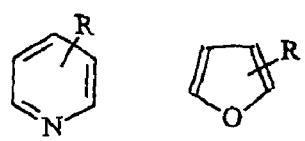

Any non-toxic nucleophile can be used in the present invention, including natural and synthetic thiols (FIG. 9). Endogenous (circulating) nitric oxide generally reacts with water, forming nitrite and nitrate. However, when a nucleophile is present, the nitric oxide is converted into a nitric oxide donor that acts the same way as nitric oxide itself, only more efficiently. The nucleophiles can be administered prior to administration of perfluorocarbons, with the perfluorocarbons, or after administration of the perfluorocarbons.

The nucleophiles are preferably low molecular weight compounds, generally less than about 5,000 Daltons, or the size of a peptide of up to about 10 amino acids, so that they can be readily incorporated into the perfluorocarbon micelles when administered with the perfluorocarbon. While thiols are among the preferred nucleophiles, one of the most preferred thiols is α-lipoic acid because of its hydrophobic tail, which contains two thiol groups at the end of the tail. Other useful thiols in the present invention include, but are not limited to, L-cysteine, N-acetyl-L-cysteine, and glutathione. Other useful low molecular weight nucleophiles are tryptophan, melatonin, serotonin, and their derivatives, and antioxidants such as α-tocopherol (FIG. 9).

Other nucleophiles that can be used as nitric oxide donors are non-toxic molecules containing iodide ion, alkyl sulfides, bromide, hydroxide, alkoxides, etc. One skilled in the art can readily determine if a substrate is an appropriate nucleophile without undue experimentation.

Administration of the perfluorocarbon compounds is in a therapeutically effective amount, i.e., that amount which corrects the particular biological problem. For inhibiting nitric oxide activity, the perfluorocarbon should be administered in amounts of at least about 0.5% w/volume of blood or more. The perfluorocarbon can be administered in larger quantities, e.g. up to about 10% w/volume of blood, depending upon the condition of the patient and the particular problem to be treated. For enhancing the effects of nitric oxide, the perfluorocarbons should be administered in amounts of less than about 0.5% w/volume of blood, and generally in amounts ranging from about 0.01% up to about 0.1% w/volume of blood. These amounts will vary with the individual and the condition to be treated.

The perfluorocarbons have a half-life in mammals of about 24-48 hours, depending upon the size of the perfluorocarbon micelle. For treating chronic conditions, the perfluorocarbons can be administered at 24-48 hour intervals, depending upon the severity of the condition and the half-life of the particular perfluorocarbon used. For treating acute conditions, of course, the perfluorocarbons can be administered once or several times, depending upon the severity of the condition and the length of time required to affect the condition.

Administration of the perfluorocarbons can be parenteral, topical, or intracavity. Intravenously may be the preferred method of parenteral administration, for example, for treatment of hypertension. Intracavity administration may be, for example, bronchial (by inhalation), cervical, uteral, or vaginal (for remedying disorders of the reproductive tract), oral (for example, held contained in a pouch or carrier for sublingual or buccal administration, or anal. Topical administration may be by incorporating the perfluorocarbon in a suitable transdermal patch, or by incorporating the perfluorocarbon in a vehicle that enhances penetration of the skin, such as DMSO.

In determining the dosages be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ID_{50}$ level of the active ingredient in question can be one of the dosage levels selected, and the other two selected to reach a toxic level. The lowest dose that dose not exhibit a biologically demonstrable effect. The toxicology tests should be repeated using appropriate new doses calculated on the basis of the results obtained. Young, healthy mice or rats belonging to a well-defined strain are the first choice of species, and the first studies generally use the preferred route of administration. Control groups given a placebo or which are untreated are included in the tests. Tests for general toxicity, as outlined above, should normally be repeated in another non-rodent species, e.g., a rabbit or dog. Studies may also be repeated using alternate routes of administration.

Singe dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds. Data on single dose toxicity, e.g., $ID_{50}$, the dosage at which half of the experimental animals die, is to be expressed in units of weight or volume per kg of body weight and should generally be furnished for at least two species with different modes of administration. In addition to the $ID_{50}$ value in rodents, it is desirable to determine the highest tolerated dose and/or lowest lethal dose for other species, i.e., dog and rabbit.

When a suitable and presumably safe dosage level has been established as outlined above, studies on the drug's chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed. Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compounds of the present invention are then ready for clinical trials to compare the efficacy of the compounds to existing therapy. A dose-response relationship to therapeutic effect and for side effects can be more finely established at this point. The amount of compounds of the present invention to be administered to any given patient must be determined empirically, and will differ depending upon the condition of the patients. Relatively small amounts of the active ingredient can be administered at first, with steadily increasing dosages if no adverse effects are noted. Of course, the maximum safe toxicity dosage as determined in routine animal toxicity tests should never be exceeded.

Perfluorocarbons are used to modulate nitric oxide activity in humans and other mammals. Perfluorocarbons can be used to treat and prevent any disease or disorder that relates to an abnormal nitric oxide activity and/or the level of nitric oxide in an animal. At low levels, when the perfluorocarbons are used as potentiators of nitric oxide activity, the effect of the perfluorocarbons is greatly enhanced by the addition of nucleophiles, particularly natural or synthetic thiols, as well as other molecules that concentrate in whole or in part into perfluorocarbon micelles, react with, and subsequently donate nitric oxide. These molecules can be administered prior to administering perfluorocarbons, simultaneously with perfluorocarbons, or in a formulation wherein the molecules are included inside the perfluorocarbon micelles during their production.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

1. Moncada, S., & Higgs, A. The L-arginine-nitric oxide pathway. *N. Engl. J. Med.* 329, 2002-2012 (1993).
2. Bredt, D. S., & Snyder S. H. Nitric oxide: a physiologic messenger molecule. *Annu. Rev. Biochem.* 63, 175-195 (1994).
3. Stamler, J. S., Singel D. J., & Loscalzo, J. Biochemistry of nitric oxide and its redox-activated forms. *Science* 258, 1898-1902 (1992).
4. Ignarro, L. J. et al. Mechanism of vascular smooth muscle relaxation by organic nitrates, nitrites, nitro-prusside, and nitric oxide: evidence for the involvement of S-nitrosthiols as active intermediates. *J. Pharmacol. Exp. Ther.* 218, 739-749 (1981).
5. Keaney J F Jr, Simon D I, Stamler J S, Jaraki O, Scharfstein J, Vita J A, & Loscalzo J. NO forms an adduct with serum albumin that has endothelium-derived relaxing factor-like properties. *J Clin Invest.* 91, 1582-1589 (1993).
6. Stamler J. S. et al. Nitric oxide circulates in mammalian plasma primarily as an S-nitroso adduct of serum albumin. *Proc Natl Acad Sci USA.* 89, 7674-7677 (1992).
7. Scharfstein J. S., Keaney J. F. Jr, Slivka A., Welch G. N., Vita J. A., Stamler J. S., & Loscalzo J. In vivo transfer of nitric oxide between a plasma protein-bound reservoir and low molecular weight thiols. *J Clin Invest.* 94, 1432-1439 (1994).
8. Jia L., Bonaventura C., Bonaventura J., & Stamler J. S. S-nitrosohaemoglobin: a dynamic activity of blood involved in vascular control. *Nature* 380, 221-226 (1996).
9. Clancy R. M., Levartovsky D., Leszczynska-Piziak J., Yegudin J., & Abramson S. B. Nitric oxide reacts with intracellular glutathione and activates the hexose monophosphate shunt in human neutrophils: evidence for S-nitrosoglutathione as a bioactive intermediary. *Proc Natl Acad Sci USA.* 91, 3680-3684 (1994).
10. Gaston B., Sears S., Woods J., Hunt J., Ponaman M., McMahon T, & Stamler J. S. Bronchodilator S-nitrosothiol deficiency in asthmatic respiratory failure. *Lancet* 351, 1317-1319. (1998).
11. Rafikova O., Rafikov R., and Nudler E. (2002) Catalysis of S-nitrosothiols formation by serum albumin: the mechanism and implication in vascular control. *Proc Natl Acad Sci USA.* 99, 5913-5918.
12. Hogg, N. Biological chemistry and clinical potential of S-nitrosothiols. *Free Radic Biol Med.* 28, 1478-1486 (2000).
13. Marzinzig M, et al. Improved methods to measure end products of nitric oxide in biological fluids: nitrite, nitrate, and S-nitrosothiols. *Nitric Oxide.* 1, 177-189 (1997).
14. Tsikas D, Sandmann J, Gutzki F M, Stichtenoth D O, & Frolich J. C. Measurement of S-nitrosoalbumin by gas chromatography-mass spectrometry. II. Quantitative determination of S-nitrosoalbumin in human plasma using S-[15N]nitrosoalbumin as internal standard. *J Chromatogr B* 726, 13-24 (1999).
15. Singh, R. J., Hogg, N., Joseph, J., & Kalyanaraman B. Mechanism of nitric oxide release from S-nitrosothiols. *J Biol Chem.* 271, 18596-18603 (1996).
16. Kashiba-Iwatsuki et al. Ascorbic acid and reducing agents regulate the fates and functions of S-nitrosothiols. *J. Biochem.* 122, 1208-1214 (1997).
17. Aleryani S, Milo E, Rose Y, & Kostka P. Superoxide-mediated decomposition of biological S-nitrosothiols. *J Biol Chem.* 273, 6041-6045 (1998).
18. Nikitovic D, & Holmgren A. S-nitrosoglutathione is cleaved by the thioredoxin system with liberation of glutathione and redox regulating nitric oxide. *J Biol Chem.* 271, 19180-19185 (1996).
19. Jourd'heuil D., Hallen K., Feelisch M., & Grisham M. B. Dynamic state of S-nitrosothiols in human plasma and whole blood. *Free Radic Biol Med.* 28, 409-417 (2000).
20. Tsikas D, Sandmann J, Luessen P, Savva A, Rossa S, Stichtenoth D O, & Frolich J C. S-Transnitrosylation of albumin in human plasma and blood in vitro and in vivo in the rat. *Biochim Biophys Acta.* 1546, 422-434 (2001).
21. Wink D. A., et al. Reaction kinetics for nitrosation of cysteine and glutathione in aerobic nitric oxide solutions at neutral pH. Insights into the fate and physiological effects of intermediates generated in the NO/O2 reaction. *Chem Res Toxicol.* 7, 519-525 (1994).
22. Lewis R. S. & Deen W. M. Kinetics of the reaction of nitric oxide with oxygen in aqueous solutions. *Chem Res Toxicol* 7, 568-574 (1994).
23. Kharitonov V. G., Sundquist A. R., & Sharma, V. S. Kinetics of nitrosation of thiols by nitric oxide in the presence of oxygen. *J Biol Chem.* 270, 28158-28164 (1995).
24. Williams D. L. Nitrosating agents: is peroxynitrite a likely candidate? *Nitric Oxide* 1, 522-527 (1997).
25. Nedospasov A., Rafikov R., Beda N., & Nudler E. An autocatalytic mechanism of protein nitrosylation. *Proc Natl Acad Sci USA.* 97, 13543-13548 (2000).
26. Liu X., Miller M. J, Joshi M. S, Thomas D. D, & Lancaster J. R. Jr. Accelerated reaction of nitric oxide with $O_2$ within the hydrophobic interior of biological membranes. *Proc Natl Acad Sci USA.* 95, 2175-2179 (1998).
27. Goss S. P., Singh R. J., Hogg N., & Kalyanaraman B. Reactions of NO, $NO_2$ and peroxynitrite in membranes: physiological implications. *Free Radic Res.* 31, 597-606 (1999).

28. Al-Sa'doni H, & Ferro A. S-Nitrosothiols: a class of nitric oxide-donor drugs. *Clin Sci (Lond)* 98, 507-520 (2000).
29. Lowe, K. C. Perfluorinated blood substitutes and artificial oxygen carriers. *Blood Reviews* 13, 171-184 (1999).
30. Lowe K. C. Perflurochemical respiratory gas carriers: applications in medicine and biotechnology. *Science Prog.* 80, 169-193 (1997).
31. Rudiger St., Grob U., & Kemnitz E. Perluorocarbons—useful tools for medicine. *Eur J Med Res* 5, 209-216 (2000).
32. Spahn D. R. Blood substitutes. Artificial oxygen carriers: perfluorocarbon emulsions. *Crit Care* 3, R93-97 (1999).
33. Gervits L. L. (1994) Perflurocarbon-based blood substitutes. Russian experience. In *Fluorine in medicine in 21st century.* (eds. Banks R. E., Lowe K. C. Shrewsbury, Rapra).
34. Beda N. V., & Suntsova T. P. Micellar catalysis for oxidation of nitric oxide (NO) in the multi-phase systems in vivo. *FEBS Lett.* 453, 229-235 (1999).
35. Beckman, J. S., & Koppenol, W. H. Nitric oxide, superoxide, and peroxynitrite: the good, the bad, and ugly. *Am J Physiol.* 271, C1424-C1437 (1996).
36. Beckman J. S., Ye Y Z, Anderson P. G., Chen M. A., Accavitti M., Tarpey M. M., & White C. R. Extensive nitration of protein tyrosines in human atherosclerosis dated by immunohistochemistry. *Biol Chem Hoppe-Sylers'* 375, 81-88 (1994).
37. Nakazawa H, Fukuyama N, Takizawa S, Tsuji C, Yoshitake M, & Ishida H. Nitrotyrosine formation and its role in various pathological conditions. *Free Radic Res.* 33, 771-784 (2000).
38. Wenzel R P, Pinsky M R, Ulevitch R J, & Young L. (1996) Current understanding of sepsis. *Clin Infect Dis.* 22, 407-412.
39. Titheradge M. A. (1999) Nitric oxide in septic shock. *Biochim Biophys Acta.* 1411, 437-455.
40. DeGroote M. A. & Fang F. C. (1999) Antimicrobial properties of nitric oxide. pp. 231-247. In *Nitric Oxide and Infection* (ed. Fang F. C., Kluwer Acad./Plenum Publishers, NY).
41. Wray G. & Thiemermann C. (1999) Nitric oxide in sepsis. pp. 265-277. In *Nitric Oxide and Infection* (ed. Fang F. C., Kluwer Acad./Plenum Publishers, NY).
42. Blantz R C, & Munger K. Role of nitric oxide in inflammatory conditions. *Nephron* 90, 373-378 (2002).
43. Keipert P. E. Perflubron emulsion (Oxygent™): a temporary intravenous oxygen carrier. *Anasthesiol Intensivemed Notfallmed Schmerzthet* 36, Suppl. 2:S104-106 (2001).
44. Baker H, Deangelis B, Baker E R, & Hutner S H. A practical assay of lipoate in biologic fluids and liver in health and disease. *Free Radic Biol Med.* 25, 473-479 (1998).
45. Ellman, G. L. *Arch. Biochem. Biophys.* 82, 70-77 (1959).
46. Saville, B. *Analyst* 83, 670-672 (1958).
47. Fox, S. C., Burgess-Wilson, M., Heptinstall, S., & Mitchell, J. R. A. Platelet aggregation in whole blood determined using the Ultra-Flo 100 platelet counter. *Thrombosis and Haemostasis,* 48, 327-329(1982).
48. Storey, R. F., Wilcox, R. G., & Heptinstall, S. Differential effects of glycoprotein IIb/IIIa antagonists on platelet microaggregate and macroaggregate formation and effect of anticoagulant on antagonist potency: implications for assay methodology and comparison of different antagonists. *Circulation,* 98, 1616-1621 (1998).
49. Bernat A, Vallee E, Maffrand J P, & Gordon J L. The role of platelets and ADP in experimental thrombosis induced by venous stasis in the rat. *Thromb Res Suppl.* 52, 65-70 (1988).
50. Maggi A, Abbadini M, Pagella P G, Borowska A, Pangrazzi J, & Donati M. B. Antithrombotic properties of dermatan sulphate in a rat venous thrombosis model. *Haemostasis* 17, 329-335 (1987).
51. Reyers I, de Gaetano G, & Donati M. B. Venostasis-induced thrombosis in rats is not influenced by circulating platelet or leukocyte number. *Agents Actions.* 28, 137-141 (1989).
52. Chabielska E, Pawlak R, Golatowski J, Rolkowski R, Pawlak D, & Buczko W. Losartan inhibits experimental venous thrombosis in spontaneously hypertensive rats. *Thromb Res.* 90, 271-278 (1998).
53. Timmermans P B, Wong P C, Chiu A T, Herblin W F, Benfield P, Carini D J, Lee R J, Wexler R R, Saye J A, & Smith R D. Angiotensin II receptors and angiotensin II receptor antagonists. *Pharmacol Rev.* 45, 205-251 (1993).
54. Forman M B, Bingham S, Kopelman H A, Wehr C, Sandler M P, Kolodgie F, Vaughn W K, Friesinger G C, & Virmani R. Reduction of infarct size with intracoronary perfluorochemical in a canine preparation of reperfusion. *Circulation* 71, 1060-1068 (1985).
55. Rice H. E., Virmani R., Hart C. L., Kolodgie f. D., & Farb A. Dose-dependant reduction of myocardial infarct size with the perfluorochemical Fluosol-DA. *Am Heart J.* 120, 1039-1046.
56. Forman M B, Ingram D A, & Murray J J. Role of perfluorochemical emulsions in the treatment of myocardial reperfusion injury. *Am Heart J.* 124, 1347-1357 (1992).
57. Wall T. C et al. Intravenous Fluosol in the treatment of acute myocardial infarction. Results of the Thrombolysis and Angioplasty in Myocardial Infarction 9 Trial. TAMI 9 Research Group. *Circulation* 90, 114-120 (1994).
58. Kloner R. A, & Hale S. Cardiovascular applications of fluorocarbons in regional ischemia/reperfusion. *Artif Cells Blood Substit Immobil Biotechnol.* 22, 1069-1081 (1994).
59. Hale S. L., Hammerman H, & Kloner R. A. Effect of two perfluorocarbon emulsions on reperfusion injury after coronary artery occlusion in rabbits. *Basic Res Cardiol.* 90, 404-409 (1995).
60. Rakhit R. D. & Marber M. S. Nitric oxide: an emerging role in cardioprotection? *Heart,* 86: 368-372 (2001).
61. Vinten-Johansen J, Zhao Z Q, Nakamura M, Jordan J E, Ronson R S, Thourani V H, & Guyton R A. Nitric oxide and the vascular endothelium in myocardial ischemia-reperfusion injury. *Ann N Y Acad Sci.* 874: 354-370 (1999).
62. Paulus W J, Vantrimpont P J, & Shah A M. Acute effects of nitric oxide on left ventricular relaxation and diastolic distensibility in humans. Assessment by bicoronary sodium nitroprusside infusion. *Circulation* 89, 2070-2078 (1994).
63. Heard S. O. & Puyama J. C. The anti-inflammatory effects of perfluorocarbons: Let's get physical. *Crit Care Med.* 28: 1241-1242 (2000).
64. Yin Z L, & Dusting G. J. A nitric oxide donor (spermine-NONOate) prevents the formation of neointima in rabbit carotid artery. *Clin Exp Pharmacol Physiol.* 24, 436-438 (1997).
65. Miyoshi H, Nakaya Y, & Moritoki H. Nonendothelial-derived nitric oxide activates the ATP-sensitive K+ channel of vascular smooth muscle cells. *FEBS Lett.* 345: 47-49 (1994).

66. Sasaki N, Sato T, Ohler A, O'Rourke B, & Marban E. Activation of mitochondrial ATP-dependent potassium channels by nitric oxide. *Circulation* 101: 439-445 (2000).

67. Napoli et al. Efficacy and age-related effects of nitric oxide-releasing aspirin on experimental restenosis. *Proc Natl Acad Sci USA*. 99, 1689-1694 (2002).

68. Maffia P, Ianaro A, Sorrentino R, Lippolis L, Maiello F M, del Soldato P, Ialenti A, & Cirino G. Beneficial effects of NO-releasing derivative of flurbiprofen (HCT-1026) in rat model of vascular injury and restenosis. *Arterioscler Thromb Vasc Biol*. 22, 263-267 (2002).

69. Min J Y, Ding B, Wang J F, Sullivan M F, & Morgan J P. Metoprolol attenuates postischemic depressed myocardial function in papillary muscles isolated from normal and postinfarction rat hearts. *Eur J Pharmacol*. 422: 115-125 (2001).

70. Bolli R. Cardioprotective function of inducible nitric oxide synthase and role of nitric oxide in myocardial ischemia and preconditioning: an overview of a decade of research. *J Mol Cell Cardiol*. 33, 1897-1918 (2001).

71. Woolfson R G, Patel V C, Neild G H, & Yellon D M. Inhibition of nitric oxide synthesis reduces infarct size by an adenosine-dependent mechanism. *Circulation* 91: 1545-1551 (1995).

72. Schulz R, & Wambolt R. Inhibition of nitric oxide synthesis protects the isolated working rabbit heart from ischaemia-reperfusion injury. *Cardiovasc Res*. 30: 432-439 (1995).

73. Johnson G 3rd, Tsao P S, & Lefer A M. Cardioprotective effects of authentic nitric oxide in myocardial ischemia with reperfusion. *Crit Care Med.*, 19: 244-252 (1991).

74. Siegfried M R, Erhardt J, Rider T, Ma X L, & Lefer A. M. Cardioprotection and attenuation of endothelial dysfunction by organic nitric oxide donors in myocardial ischemia-reperfusion. *J Pharmacol Exp Ther*. 260: 668-675 (1992).

75. Pabla R, Buda A J, Flynn D M, Salzberg D B, & Lefer D J. Intracoronary nitric oxide improves postischemic coronary blood flow and myocardial contractile function. *Am J Physiol*. 269: H1113-H1121 (1995).

76. Pabla R, Buda A J, Flynn D M, Blesse S A, Shin A M, Curtis M J, & Lefer D. J. Nitric oxide attenuates neutrophil-mediated myocardial contractile dysfunction after ischemia and reperfusion. *Circ Res*. 78: 65-72 (1996).

77. Murry C. E., Jennings R. B., & Reimer K. A. Preconditioning with ischemia: a delay of lethal cell injury in ischemic myocardium. *Circulation* 74, 1124-1136 (1986).

78. Kuzuya T, Hoshida S, Yamashita N, Fuji H, Oe H, Hori M, Kamada T, & Tada M. Delayed effects of sublethal ischemia on the acquisition of tolerance to ischemia. *Circ Res*. 72:1293-1299 (1993).

79. Marber M S, Latchman D S, Walker J M, & Yellon D. M. Cardiac stress protein elevation 24 hours after brief ischemia or heat stress is associated with resistance to myocardial infarction. *Circulation* 88:1264-1272 (1993).

80. Bolli R. The early and late phases of preconditioning against myocardial stunning and the essential role of oxyradicals in the late phase: an overview. *Basic Res Cardiol*. 91: 57-63 (1996).

81. Xi L, Rakesh C., & Kukreja R. C. Pivotal role of nitric oxide in delayed pharmacological preconditioning against myocardial infarction. *Toxicology* 155: 37-44 (2000).

82. Bolli R. The late phase of preconditioning. *Circ Res*. 87: 972-983 (2000).

83. Yamashita N, Hoshida S, Taniguchi N, Kuzuya T, & Hori M. A "second window of protection" occurs 24 h after ischemic preconditioning in the rat heart. *J Mol Cell Cardiol*. 30: 1181-1191 (1998).

84. Qiu Y, Rizvi A, Tang X L, Manchikalapudi S, Takano H, Jadoon A K, Wu W J, & Bolli R. Nitric oxide triggers late preconditioning against myocardial infarction in conscious rabbits. *Am J Physiol*. 1997 December; 273(6 Pt 2):H2931-6.

85. Richardson, et al. Potential therapeutic uses for S-nitrosothiols. Clin Sci (Lond). 102, 99-105).

86. Poli G. Introduction-serial review: reactive oxygen and nitrogen in inflammation (2002). Free Radic Biol Med. 33, 301-312.

87. Kojda, et al. Regulation of basal mycardial function by NO. Cardiovascular Research. 41:514-523, (1999).

88. Richardson, et al. Potential therapeutic uses for S-nitrosothiols. Clinical Science. 102:99-105, (2002).

89. Al-Sa'Doni, et al. S-Nitrosothiols: a class of nitric oxide-donor drugs. Clinical Science. 98:507-520, (2000).

90. Southan, et al. Selective Pharmacological Inhibition of Distinct Nitric Oxide Synthase Isoforms. Biochemical Pharmacology. 51:383-394, (1996).

91. Gabbai. Effects of nitric oxide synthase blockers on renal function. Nephrol. Dial. Transplant. 16(Suppl 1):10-13, (2001).

92. Feihl, et al. Is nitric oxide overproduction the target of choice for the management of septic shock? Pharmacology & Therapeutics. 91:179-213, (2001).

93. U.S. Pat. No. 6,204,296, published Mar. 20, 2001: Weers, et al.

94. U.S. Pat. No. 6,289,892, published Sep. 18, 2001: Faithfull, et al.

95. U.S. Pat. No. 6,166,092, published Dec. 26, 2000: Sekins, et al.

96. U.S. Pat. No. 5,684,050, published Nov. 4, 1997: Clark, Jr. et al.

97. U.S. Pat. No. 5,514,720, published May 7, 1996: Clark, Jr. et al.

98. U.S. Pat. No. 5,621,144, published Apr. 15, 1997: Cooper

99. U.S. Pat. No. 5,869,539, published Feb. 9, 1999: Garfield, et al.

What is claimed is:

1. A method for controlling metabolism of nitric oxide comprising administrating to an animal in need thereof effective amount of a perfluorocarbon having a molecular weight of from about 400 Dalton to about 700 Dalton, wherein said animal is suffering from at least one disease or condition selected from the group consisting of hypotension, vasoplegia, vasoconstriction, vasorelaxation, thrombosis, blood clotting endotoxic shock and septic shock, restenosis after angioplasty, ischemic perfusion injury and preeclampsia.

2. The method according to claim 1 wherein the perfluorocarbon is administered in an amount of at least about 0.5% w/volume of blood to inhibit nitric oxide activity.

3. The method according to claim 1 wherein the perfluorocarbon is administered in an amount of less than about 0.5% w/volume of blood to enhance nitric oxide activity.

4. The method according to claim 3 wherein the perfluorocarbon is administered in an amount of from about 0.01% to about 0.1% w/volume of blood to enhance nitric oxide activity.

5. The method according to claim 3 wherein at least one nucleophile is administered in conjunction with the perfluorocarbon.

6. The method according to claim 5 wherein the nucleophile is a thiol or mixture of thiols.

7. The method according to claim 6 wherein the thiol is α-lipoic acid, L-cysteine, or glutathione.

8. The method according to claim 2 comprising treating hypotension and vasoplegia.

9. The method according to claim 3 comprising treating vasorelaxation.

10. The method according to claim 3 comprising treating blood clotting and thrombosis.

11. The method according to claim 3 comprising suppressing restenosis after angioplasty.

12. The method according to claim 3 comprising treating preeclampsia.

13. A method for treating microbial or viral infections comprising administering to an animal in need thereof an effective amount of a perfluorocarbon and an optional nucleophile.

14. The method according to claim 13 wherein the viral infections are selected from the group consisting of rhinoviral infections and retroviral infections.

15. A method for treating leukemia comprising administering an effective amount of a perfluorocarbon to a patient in need thereof.

16. The method according to claim 1 wherein the perfluorocarbon is in an emulsion, wherein the particle size of the perfluorocarbon ranges from about 25 nm to about 1 micron.

* * * * *